US011402391B2

(12) United States Patent
Patterson et al.

(10) Patent No.: US 11,402,391 B2
(45) Date of Patent: Aug. 2, 2022

(54) METHODS OF TREATING A LONG-HAULER SUBJECT FOR CHRONIC COVID-19 BY ADMINISTERING A CCR5 OR CCL5 ANTAGONIST

(71) Applicant: IncellDx, Inc., San Carlos, CA (US)

(72) Inventors: Bruce K. Patterson, Menlo Park, CA (US); Edgar B. Francisco, San Carlos, CA (US); Amruta Pise, San Carlos, CA (US); Emily Long, San Carlos, CA (US)

(73) Assignee: IncellDx, Inc., San Carlos, CA (US)

( * ) Notice: Subject to any disclaimer, the term of this patent is extended or adjusted under 35 U.S.C. 154(b) by 0 days.

(21) Appl. No.: 17/351,055

(22) Filed: Jun. 17, 2021

(65) Prior Publication Data

US 2021/0373034 A1    Dec. 2, 2021

Related U.S. Application Data

(60) Provisional application No. 63/128,471, filed on Dec. 21, 2020, provisional application No. 63/166,704, filed on Mar. 26, 2021.

(51) Int. Cl.
| | |
|---|---|
| *C07K 16/28* | (2006.01) |
| *A61K 38/19* | (2006.01) |
| *G01N 33/68* | (2006.01) |
| *A61K 45/06* | (2006.01) |
| *A61K 31/506* | (2006.01) |
| *A61K 31/46* | (2006.01) |
| *A61K 31/4178* | (2006.01) |

(52) U.S. Cl.
CPC ..... *G01N 33/6893* (2013.01); *A61K 31/4178* (2013.01); *A61K 31/46* (2013.01); *A61K 31/506* (2013.01); *A61K 38/195* (2013.01); *A61K 45/06* (2013.01); *C07K 16/2866* (2013.01); *C07K 2317/24* (2013.01); *G01N 2333/521* (2013.01); *G01N 2800/52* (2013.01)

(58) Field of Classification Search
CPC .............. A61K 38/195; C07K 16/2866; C07K 2317/24
See application file for complete search history.

(56) References Cited

U.S. PATENT DOCUMENTS

| | | | |
|---|---|---|---|
| 11,045,546 B1 | 6/2021 | Kelly et al. | |
| 2005/0220790 A1 | 10/2005 | Proost et al. | |
| 2006/0165650 A1 | 7/2006 | Pavone et al. | |
| 2009/0148455 A1 | 6/2009 | Fischer et al. | |
| 2012/0077733 A1 | 3/2012 | Weber et al. | |
| 2012/0201826 A1 | 8/2012 | Fischer et al. | |
| 2013/0303512 A1 | 11/2013 | Pestell | |
| 2014/0109245 A1 | 4/2014 | Pestell | |
| 2014/0377278 A1 | 12/2014 | Elinav et al. | |
| 2015/0079099 A1 | 3/2015 | Fischer et al. | |
| 2017/0231991 A1 | 8/2017 | Pestell | |
| 2018/0303830 A1 | 10/2018 | Pestell et al. | |
| 2021/0032355 A1 | 2/2021 | Francisco et al. | |
| 2021/0373034 A1 | 12/2021 | Patterson et al. | |

OTHER PUBLICATIONS

Mathew D, et al. (Sep. 4, 2020). 369 (6508):1-17. (doi: 10.1126/science.abc8511).*
Olson et al. Curr Opin HIV AIDS, Mar. 2009;4(2):104-111.
Adedeji et al., Novel Inhibitors of Severe Acute Respiratory Syndrome Coronavirus Entry That Act by Three Distinct Mechanisms, Journal of Virology, Jul. 2013, vol. 87, No. 14, p. 8017-8028.
Basu et al., Novel Small Molecule Entry Inhibitors of Ebola Virus, The Journal of Infectious Diseases, Oct. 2015, vol. 212, Suppl. 2, p. S425-S434.
Carrol et al., The Role of RANTES in Meningococcal Disease, The Journal of Infectious Diseases, Jul. 2000, vol. 182, No. 1, p. 363-366.
John et al., Low Levels of RANTES Are Associated with Mortality in Children with Cerebral Malaria, The Journal of Infectious Diseases, Sep. 2006, vol. 194, No. 6, p. 837-845.
Kandeel et al., Small Molecule Inhibitors of Middle East Respiratory Syndrome Coronavirus Fusion by Targeting Cavities on Heptad Repeat Trimers, Biomolecules & Therapeutics, Mar. 2020, vol. 28, No. 4, p. 311-319.
Papa et al., Cytokines as Biomarkers of Crimean-Congo Hemorrhagic Fever, Journal of Medical Virology, Jan. 2016, vol. 88, No. 1, p. 21-27.
Reddy et al., Correlation of Plasma Viral Loads and Presence of Chikungunya IgM Antibodies with Cytokine/Chemokine Levels During Acute Chikungunya Virus Infection, Journal of Medical Virology, Aug. 2014, vol. 86, No. 8, p. 1393-1401.
Reynolds et al., Ebola and Marburg Virus Vaccines, Virus Genes, Apr. 2017, vol. 53, p. 501-515.
Sun et al., Host Cytokine Storm Is Associated With Disease Severity of Severe Fever With Thrombocytopenia Syndrome, The Journal of Infectious Diseases, Oct. 2012, vol. 206, No. 7, p. 1085-1094.
Akalin et al., Covid-19 and Kidney Transplantation, The New England Journal of Medicine, Apr. 24, 2020, URL=http://www.nejm.org/doi/full/10.1056/NEJMc2011117, and the Supplement to: Akalin E, Azzi Y, Bartash R, et al., Covid-19 and kidney transplantation, N Engl J Med 2020;382:2475-7. DOI: 10.1056/NEJMc2011117, 11 pages.

(Continued)

*Primary Examiner* — Robert S Landsman
(74) *Attorney, Agent, or Firm* — Shweta Chandra; Bret E. Field; Bozicevic, Field & Francis LLP

(57) ABSTRACT

Methods of assigning a COVID pathological type for a subject suffering from COVID-19 are provided. Aspects of the methods include assigning a COVID pathological type for the subject based on a determined quantitative, multiplex cytokine/chemokine panel in a test sample from the subject. Also provided are methods of treating a subject (e.g., a long hauler subject) for chronic COVID-19. Aspects of such methods include administering to the long hauler subject a CCR5/CCL5 interaction inhibitor to treat the long hauler subject. Also provided are compositions for use in practicing the methods. The methods and compositions find use in a variety of applications, including patient stratification, treatment and therapy determination and therapy response assessment.

18 Claims, 4 Drawing Sheets

(56) References Cited

OTHER PUBLICATIONS

U.S. National Library of Medicine, Study to Evaluate the Efficacy and Safety of Leronlimab for Mild to Moderate COVID-19, Apr. 13, 2020, URL=https://clinicaltrials.gov/ct2/show/NCT04343651, 9 pages.
Liu et al., Design, Synthesis and Biological Evaluation of Novel Piperazine Derivatives as CCR5 Antagonists, PLOS One, Jan. 2013, vol. 8, No. 1, e53636, p. 1-7.
Okamoto et al., The chemokine receptor antagonist cenicriviroc inhibits the replication of SARS-CoV-2 in vitro, Antiviral Research, Jul. 2020, vol. 182, 104902, p. 1-6.
Wang et al., SARS-CoV-2: Structure, Biology, and Structure-Based Therapeutics Development, Frontiers in Cellular and Infection Microbiology, Nov. 2020, vol. 10, Article 587269, p. 1-17.
Iannaccone et al., Weathering the Cytokine Storm in COVID-19: Therapeutic Implications, CardioRenal Medicine, Jun. 2020, vol. 10, p. 277-287.
CytoDyn, Inc., Leronlimab Under Evaluation for Potential Treatment of Coronavirus: CytoDyn and IncellDX in discussions with potential partners about the use of leronlimab to treat 2019 Novel Coronavirus (2019-nCoV), Jan. 28, 2020, 4 pages.
Huang et al., An Interferon-gamma-Related Cytokine Storm in SARS Patients, Journal of Medical Virology, Feb. 2005, vol. 75, No. 2, p. 185-194.
Ruiz-Mateos et al., Virological Response after Short-Term CCR5 Antagonist Exposure in HIV-Infected Patients: Frequency of Subjects with Virological Response and Associated Factors, Antimicrobial Agents and Chemotherapy, Oct. 2011, vol. 55, No. 10, p. 4664-4669.
Baba et al., TAK-652 Inhibits CCR5-Mediated Human Immunodeficiency Virus Type 1 Infection In Vitro and Has Favorable Pharmacokinetics in Humans, Antimicrobial Agents and Chemotherapy, Nov. 2005, vol. 49, No. 11, p. 4584-4591.
Kim et al., CCR5 receptor antagonists in preclinical to phase II clinical development for treatment of HIV, Expert Opinion on Investigational Drugs, Nov. 2016, vol. 25, No. 12, p. 1377-1392.
Pulley, CCR5 antagonists: from discovery to clinical efficacy, Chemokine Biology—Basic Research and Clinical Application, vol. II, edited by Kuldeep Neote, Gordon L. Letts and Bernhard Moser, 2007, p. 145-163.
Schall et al., Overcoming hurdles in developing successful drugs targeting chemokine receptors, Nature Reviews—Immunology, May 2011, vol. 11, p. 355-363.
Ye et al., The pathogenesis and treatment of the 'Cytokine Storm' in COVID-19, Journal of Infection, Apr. 2020, vol. 80, p. 607-613.
Liu et al., Maraviroc Attenuates Trauma-Hemorrhage-Induced Hepatic Injury through PPAR Gamma-Dependent Pathway in Rats, PLOS One, Oct. 2013, vol. 8, No. 10, p. 1-7.
Di Paola et al., Peroxisome Proliferator-Activated Receptors and Acute Lung Injury, Hindawi Publishing Corporation, PPAR Research, May 2007, Art. 63745, p. 1-8.
Huang et al., Clinical features of patients infected with 2019 novel coronavirus in Wuhan, China, The Lancet, Feb. 2020, vol. 395, p. 497-506, and its Supplementary Appendix, 7 pages.
Zhao et al., Longitudinal COVID-19 profiling associates IL-1RA and IL-10 with disease severity and RANTES with mild disease, JCI Insight, Jun. 2020, vol. 5, No. 13, p. 1-11.
Balnis et al., Unique inflammatory profile is associated with higher SARS-CoV-2 acute respiratory distress syndrome (ARDS) mortality, Am J. Physiol Regul. Integr. Comp. Physiol., Jan. 2021, vol. 320, p. 1-20.
Horspool et al., Interplay of Antibody and Cytokine Production Reveals CXCL13 as a Potential Novel Biomarker of Lethal SARS-CoV-2 Infection, mSphere, Jan./Feb. 2021, vol. 6, No. 1, p. 1-14.
Channappanavar et al., Pathogenic human coronavirus infections: causes and consequences of cytokine storm and immunopathology, Semin Immunopathol, May 2017, vol. 39, p. 529-539.
Jacobson et al., Anti-HIV-1 Activity of Weekly or Biweekly Treatment with Subcutaneous PRO 140, a CCR5 Monoclonal Antibody, The Journal of Infectious Diseases, May 2010, vol. 201, No. 10, p. 1481-1487.
Yen et al., Modeling the Early Events of Severe Acute Respiratory Syndrome Coronavirus Infection In Vitro, Journal of Virology, Mar. 2006, vol. 80, No. 6, p. 2684-2693.
Canavese et al., Therapeutic Efficacy and Immunological Response of CCL5 Antagonists in Models of Contact Skin Reaction, PLoS ONE, Jan. 2010, vol. 5, No. 1, e8725, p. 1-11.
Cambien et al., CCL5 Neutralization Restricts Cancer Growth and Potentiates the Targeting of PDGFRb in Colorectal Carcinoma, PLoS ONE, Dec. 2011, vol. 6, No. 12, e28842, p. 1-11.
Chi et al., Serum Cytokine and Chemokine Profile in Relation to the Severity of Coronavirus Disease 2019 in China, The Journal of Infectious Diseases, Sep. 2020, vol. 222, p. 746-754.
Low et al., A Cytokine-based model for the pathophysiology of Long COVID symptoms, OSF Preprints, Nov. 2020, DOI:10.31219/osf.io/7gcnv, p. 1-47.
Bonny et al., Cytokine and Chemokine Levels in Coronavirus Disease 2019 Convalescent Plasma, Open Forum Infectious Diseases, Feb. 2021, vol. 8, No. 2, p. 1-10.
Jiang et al., Characterization of Cytokine/Chemokine Profiles of Severe Acute Respiratory Syndrome, Am J Respir Crit Care Med, Jan. 2005, vol. 171, p. 850-857.
Del Valle et al., An inflammatory cytokine signature predicts COVID-19 severity and survival, Nature Medicine, Oct. 2020, vol. 26, p. 1636-1643.
Patterson et al., Immune-Based Prediction of COVID-19 Severity and Chronicity Decoded Using Machine Learning, Frontiers in Immunology, Jun. 2021, vol. 12, Art. 700782, p. 1-13.

\* cited by examiner

SARS-CoV2 positive cells (blue)

METHODS OF TREATING A LONG-HAULER SUBJECT FOR CHRONIC COVID-19 BY ADMINISTERING A CCR5 OR CCL5 ANTAGONIST

CROSS-REFERENCE TO RELATED APPLICATIONS

Pursuant to 35 U.S.C. § 119 (e), this application claims priority to the filing dates of U.S. Provisional Patent Application Ser. No. 63/128,471 filed Dec. 21, 2020, and 63/166,704 filed Mar. 26, 2021, the disclosures of which applications are herein incorporated by reference.

INTRODUCTION

Severe acute respiratory syndrome coronavirus 2 (SARS-CoV-2), the causative agent of coronavirus disease 2019 was first reported in December 2019. Since the initial cases of COVID-19 were reported from Wuhan, China in December 2019 (Huang, C. et al. Clinical features of patients infected with 2019 novel coronavirus in Wuhan, China. Lancet 395, 497-506 (2020)), SARS-CoV-2 has emerged as a global pandemic with an ever-increasing number of severe cases requiring invasive external ventilation that threatens to overwhelm health care systems (World Health Organization. Coronavirus disease (COVID-2019) situation reports. See website made up of "https://www." before "who.int/emergencies/disease/novel-coronavirus-2019/situation-reports"). While it remains unclear why COVID-19 patients experience a spectrum of clinical outcomes ranging from asymptomatic to severe disease, the salient features of COVID-19 pathogenesis and mortality are rampant inflammation and CRS leading to ARDS (Mehta, P. et al. COVID-19: consider cytokine storm syndromes and immunosuppression. Lancet 395, 1033-1034 (2020); Qin, C. et al. Dysregulation of immune response in patients with COVID-19 in Wuhan, China. Clin. Infect. Dis. (2020)). Indeed, excessive immune cell infiltration into the lung, cytokine storm, and ARDS have previously been described as defining features of severe disease in humans infected with the closely related betacoronaviruses SARS-CoV and MERS-CoV (Channappanavar, R. & Perlman, S. Pathogenic human coronavirus infections: causes and consequences of cytokine storm and immunopathology. Semin Immunopathol 39, 529-539 (2017); Nicholls, J. M. et al. Lung pathology of fatal severe acute respiratory syndrome. Lancet 361, 1773-1778 (2003)).

Chronic COVID-19 refers to a group of previously infected individuals, so called "Long Haulers", who experience a multitude of symptoms from several weeks to months after recovering from their acute illness and presumably months after viral clearance. These symptoms include joint pain, muscle aches, fatigue, "brain fog" and others. These symptoms can commonly resemble rheumatic diseases such as rheumatoid arthritis, autoimmune disorders, and others such as fibromyalgia and chronic fatigue syndrome (Chen et al., "Inflammatory responses and inflammation-associated diseases in organs", Oncotarget 9, 7204-7218 (2018)). Many of these common disorders are caused by inflammation, hyper- and/or auto-immunity and some such as chronic fatigue are associated with viral persistence after an acute infection with pathogens such as Epstein Barr and Cytomegalovirus (Rasa et al., "Chronic viral infections in myalgic encephalomyelitis/chronic fatigue syndrome (ME/CFS)", J Transl Med 16, 268 (2018)). Recent studies including those from our laboratory have suggested that (CC) may be caused by persistent COVID itself (Mudd et al., "SARS-CoV-2 viral RNA shedding for more than 87 days in an individual with an impaired CD8+ T-cell response", Front Immunol (in press)).

SUMMARY

The inventors have realized that it would be desirable to identify immunologic signatures of COVID-19 severity and to determine whether Chronic COVID-19 might represent a distinct immunologic entity compared to mild to moderate (MM) or severe/critical COVID-19. The inventors have also realized that it would be desirable to determine whether the immunologic profile represents an immune response indicative of prolonged or chronic antigenic exposure. Using machine learning, the inventors have identified algorithms that allow for accurate determination of chronic COVID and severe COVID immunotypes. Further, the inventors have developed a quantitative immunologic score that may be employed to stratify patients to therapy and/or non-subjectively measure response to therapy.

Methods of assigning a COVID pathological type for a subject suffering from COVID-19 are provided. Aspects of the methods include assigning a COVID pathological type for the subject based on a determined quantitative, multiplex cytokine/chemokine panel in a test sample from the subject. Also provided are methods of treating a subject (e.g., a long hauler subject) for chronic COVID-19. Aspects of such methods include administering to the long hauler subject a CCR5/CCL5 interaction inhibitor to treat the long hauler subject. Also provided are compositions for use in practicing the methods. The methods and compositions find use in a variety of applications, including patient stratification, therapy determination, treatment and therapy response assessment.

DEFINITIONS

Figure 1:
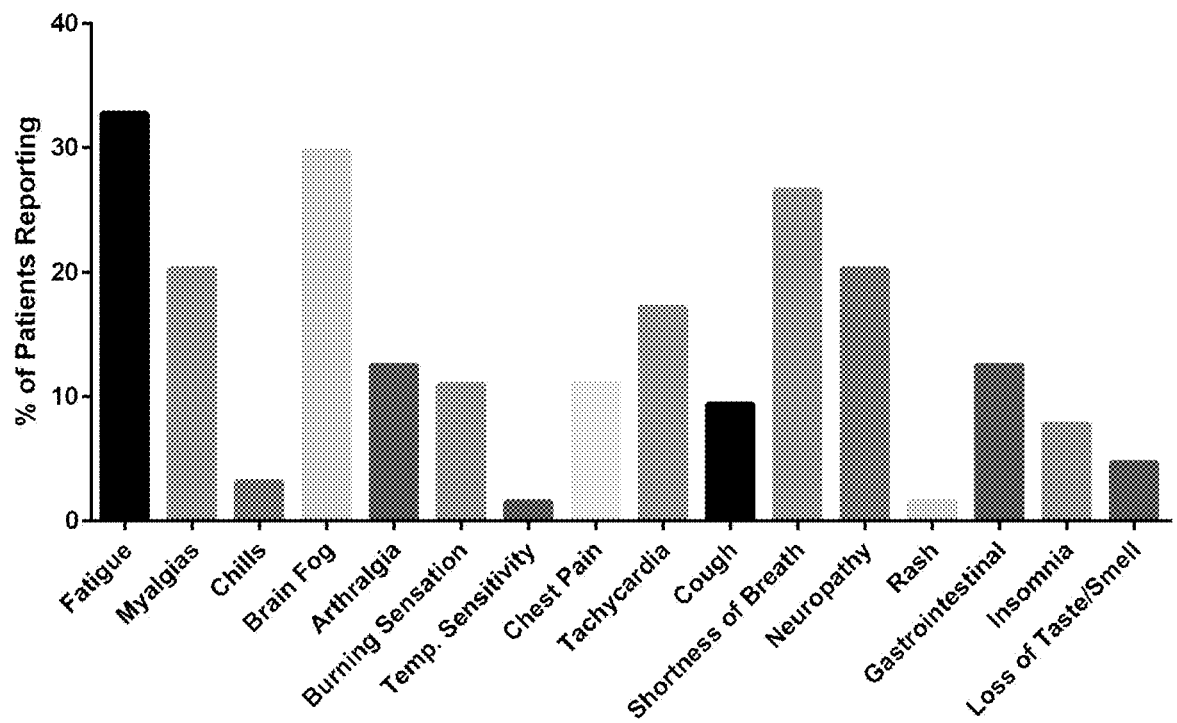
FIG. 1 graphically presents symptoms reported by long hauler patients enrolled in the study.

As used herein, the term "severity of a disease" refers to the risk posed by the disease to a subject. Severity of a disease also dictates the extent of treatment necessary for appropriately treating the subject. For example, a disease can be mild, moderate, severe, or critical.

A mild disease may cause slight discomfort and may resolve without any treatment, for example, where a subject's immune system neutralizes the disease. A moderate disease may cause more than slight discomfort and may require some treatment for the disease to resolve. A severe disease causes significant discomfort and would require extensive treatment. A critical disease is life threatening and would require hospitalization and extensive treatment, which may not be successful resulting in the subject's death.

Acute respiratory distress syndrome (ARDS) is a respiratory failure caused by rapid and widespread inflammation in the lungs. In ARDS, fluid builds up in the alveoli thereby preventing the lungs from filling with enough air and reduced oxygen supply to the organs.

The term "specific binding" refers to a direct association between two molecules, due to, for example, covalent, electrostatic, hydrophobic, and ionic and/or hydrogen-bond interactions, including interactions such as salt bridges and water bridges. A specific binding member describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organization of the other member of the pair of molecules. Thus, the members of the pair have the property of binding specifically to each other. Examples of pairs of specific binding members are antigen-antibody, biotin-avidin, hormone-hormone receptor, receptor-ligand, enzyme-substrate. Specific binding members of a binding pair exhibit high affinity and binding specificity for binding with the each other. Typically, affinity between the specific binding members of a pair is characterized by a $K_d$ (dissociation constant) of $10^{-6}$ M or less, such as $10^{-7}$ M or less, including $10^{-8}$ M or less, e.g., $10^{-9}$ M or less, $10^{-19}$ M or less, $10^{-11}$ M or less, $10^{-12}$ M or less, $10^{-13}$ M or less, $10^{-14}$ M or less, including $10^{-15}$ M or less. "Affinity" refers to the strength of binding, increased binding affinity being correlated with a lower KD. In an embodiment, affinity is determined by surface plasmon resonance (SPR), e.g. as used by Biacore systems. The affinity of one molecule for another molecule is determined by measuring the binding kinetics of the interaction, e.g. at 25° C. "Affinity" refers to the strength of binding, increased binding affinity being correlated with a lower KD. In an embodiment, affinity is determined by surface plasmon resonance (SPR), e.g. as used by Biacore systems. The affinity of one molecule for another molecule is determined by measuring the binding kinetics of the interaction, e.g. at 25° C.

DETAILED DESCRIPTION

Methods of assigning a COVID pathological type for a subject suffering from COVID-19 are provided. Aspects of the methods include assigning a COVID pathological type for the subject based on a determined quantitative, multiplex cytokine/chemokine panel in a test sample from the subject. Also provided are methods of treating a subject (e.g., a long hauler subject) for chronic COVID-19. Aspects of such methods include administering to the long hauler subject a CCR5/CCL5 interaction inhibitor to treat the long hauler subject. Also provided are compositions for use in practicing the methods. The methods and compositions find use in a variety of applications, including patient stratification, therapy determination, treatment and therapy response assessment.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Methods of Assigning a COVID Pathological Type

As summarized above, methods of assigning a COVID pathological type for a subject suffering from COVID-19 are provided. As the subject for which a pathological type is assigned by the subject methods is one suffering from COVID-19, the subject is a human individual that is experiencing one or more disease symptoms caused by SARS-CoV-2 infection, where such symptoms include, but are not limited to: fever, dry cough, shortness of breath, loss of smell, fatigue, myalgias, nausea, vomiting or diarrhea, headache, weakness, acute respiratory distress syndrome, acute cardiac injury, acute kidney injury and shock, etc. By assigning a COVID pathological type is meant stratifying or classifying, a subject suffering from COVID-19 into a defined COVID-19 symptom category, e.g., mild, moderate, severe, critical, or chronic/long COVID. A severe form of COVID-19 may show one or more of the following symptoms: severe tiredness, high fever, cough, breathlessness even at rest, painful breathing, loss of appetite, loss of thirst, sore throat, muscle ache, headache, diarrhea, and confusion. Severe form of COVID-19 would typically require significant intervention for managing symptoms, such as: pneumonia, hypoxemic respiratory failure, ARDS, sepsis, septic shock, cardiomyopathy, arrhythmia, acute kidney injury, and complications from prolonged hospitalization including secondary bacterial infections, thromboembolism, gastrointestinal bleeding, and critical illness polyneuropathy/myopathy. A critical form of COVID-19 may show of one or more of: severe tiredness, high fever, cough, breathlessness even at rest, painful breathing, loss of appetite, loss of thirst, sore throat, muscle ache, headache, diarrhea, confusion, severe pneumonia, ARDS, sepsis, organ failure, coma, and death. Critical form of COVID-19 requires hospitalization for managing symptoms such as: pneumonia, ARDS, sepsis, septic shock, cardiomyopathy, arrhythmia, acute kidney injury, and complications from prolonged hospitalization including secondary bacterial infections, thromboembolism, gastrointestinal bleeding, and critical illness polyneuropathy/myopathy. Ventilator assisted breathing may be required. Chronic or long COVID refers to a group of previously infected individuals, so called "Long Haulers", who experience a multitude of symptoms from several weeks to months after recovering from their acute illness and presumably months after viral clearance. These symptoms include joint pain, muscle aches, fatigue, "brain fog" and others. These symptoms can commonly resemble rheumatic diseases such as rheumatoid arthritis, autoimmune disorders, and others such as fibromyalgia and chronic fatigue syndrome (Chen et al., "Inflammatory responses and inflammation-associated diseases in organs", Oncotarget 9, 7204-7218 (2018)).

Aspects of the methods include assigning a COVID pathological type, e.g. severe-COVID, critical-COVID or long-COVID, for the subject based on a determined quantitative, multiplex cytokine/chemokine panel in a test sample from the subject. A determined quantitative, multiplex cytokine/chemokine panel means an evaluation or measurement of the amount a plurality of distinct cytokines and/or chemokines in a test sample from the subject. The number of cytokines and/or chemokines that are measured in the multiplex quantitative determination may vary, and in some instances ranges from two to forty, such as three to twenty, e.g., three to fifteen. The term "cytokine" is employed in its conventional sense to refer to small secreted proteins released by cells that have a specific effect on the interactions and communications between cells. The term chemokine is employed in its conventional sense to refer to cytokines produced by various cells (as at sites of inflammation) that stimulate chemotaxis in white blood cells (such as neutrophils and T cells). Cytokines/chemokines of interest that may be measured in the test sample in a given method of the invention may vary, where cytokines/chemokines that may be measured include, but are not limited to: TNF-α, IL-4, IL-13, IL-2, GM-CSF, sCD40L, CCL5 (RANTES), CCL3 (MIP-1α), IL-6, IL-10, IFN-γ, VEGF, IL-8, and CCL4 (MIP-1β).

The cytokines/chemokines that are assessed in a given panel may vary depending on the pathological type to be determined. For example, where the subject is to be evaluated for a long/chronic pathological type, the multiplex cytokine/chemokine panel may include three or more cytokines and/or chemokines, such as three to five cytokines and/or chemokines. In such instances, the cytokines and/or chemokines may vary, where in some instances the cytokines and/or chemokines are IFN-γ, IL-2 and CCL4 (MIP-1β). In some instances, the determined, quantitative, multiplex cytokine/chemokine panel may be presented as a score that is specific for chronic COVID-19 patients, i.e., such that it identifies patients with a long or chronic COVID pathological type. By score is meant a single number or value that may be used to determine the pathological type of the subject. Where such a score is employed, in some instances the score S1=(IFN-gamma+IL-2)/CCL4-MIP-1β is employed, where in some instances a score of 0.4 or greater, such as 0.5 or greater, e.g., 0.6 or greater, indicates chronic-COVID (e.g., long hauler) pathological type. In other embodiments where the subject is to be evaluated for a severe or critical pathological type, the multiplex cytokine/chemokine panel may include five or more cytokines and/or chemokines, such as five to ten cytokines and/or chemokines. In such instances, the cytokines and/or chemokines may vary, where in some instances the cytokines and/or chemokines are IL-10, IL-6, IL-13, IL-2 and IL-8. In some instances, the determined, quantitative, multiplex cytokine/chemokine panel may be presented as a score that is specific for severe or critical COVID-19 patients, i.e., such that it identifies patients with a severe or critical COVID pathological type. Where such a score is employed, in some instances the score S2=(10*IL-10+IL-6)−(IL-2+IL-8) is employed, where in some instances a score of 0 or greater, such as 0.1 or greater, e.g., 0.2 or greater, indicates sever or critical-COVID (e.g., long hauler) pathological type. In some instances, the method includes determining a score that is specific for either chronic or severe/critical COVID, e.g., S1 or S2 above, from a determined quantitative, multiplex cytokine/chemokine panel that is inclusive of all the individual cytokines/chemokines employed in a given score. In such instances, the a determined quantitative, multiplex cytokine/chemokine panel may include quantitative measurements of the amounts of three to twenty, e.g., three to fifteen, different cytokines/chemokines in the test sample, and a score, e.g., S1 or S2 as described above, is determined from the obtained measurements. For example, in some embodiments the amounts of two or more of, such as three or more of, including five or more of, e.g., ten or more of, including all of TNF-α, IL-4, IL-13, IL-2, GM-CSF, sCD40L, CCL5 (RANTES), CCL3 (MIP-1α), IL-6, IL-10, IFN-γ, VEGF, IL-8, and CCL4 (MIP-1β), are measured.

Embodiments of the methods may include obtaining the determined quantitative, multiplex cytokine/chemokine panel for the test sample from the subject. Any convenient method of determining amounts of the cytokines/chemokines in the test sample may be employed, where various methods of determining amounts of cytokines/chemokines in a sample are known in the art and can be used in the methods disclosed herein. Certain such methods include, but are not limited to, flow cytometry, mass spectrometry, protein array analysis, Western blot analysis, enzyme-linked immunosorbent assay (ELISA), and radio-immune assay (RIA).

In certain embodiments, determining the level of cytokines/chemokines of interest in the test sample is performed by flow cytometry. Flow cytometry is a methodology using multi-parameter data for identifying and distinguishing between different particle (e.g., bead) types i.e., particles that vary from one another in terms of label (wavelength, intensity), size, etc., in a fluid medium. In flow cytometrically analyzing a sample, an aliquot of the sample is first introduced into the flow path of the flow cytometer. When in the flow path, the particles in the sample are passed substantially one at a time through one or more sensing regions, where each of the cells is exposed separately and individually to a source of light at a single wavelength (or in some instances two or more distinct sources of light) and measurements of cellular parameters, e.g., light scatter parameters, and/or marker parameters, e.g., fluorescent emissions, as desired, are separately recorded for each cell. The data recorded for each cell is analyzed in real time or stored in a data storage and analysis means, such as a computer, for later analysis, as desired.

In flow cytometry-based methods, particles, e.g., beads, are passed, in suspension, substantially one at a time in a flow path through one or more sensing regions where in each region each cell is illuminated by an energy source. The energy source may include an illuminator that emits light of a single wavelength, such as that provided by a laser (e.g., He/Ne or argon) or a mercury arc lamp or an LED with appropriate filters. For example, light at 488 nm may be used as a wavelength of emission in a flow cytometer having a single sensing region. For flow cytometers that emit light at two distinct wavelengths, additional wavelengths of emission light may be employed, where specific wavelengths of interest include, but are not limited to: 405 nm, 535 nm, 561 nm, 635 nm, 642 nm, and the like. Following excitation of a labeled specific binding member bound to a polypeptide by an energy source, the excited label emits fluorescence and the quantitative level of the polypeptide on each cell may be detected, by one or more fluorescence detectors, as it passes through the one or more sensing regions.

In flow cytometry, in addition to detecting fluorescent light emitted from particles labeled with fluorescent markers, detectors, e.g., light collectors, such as photomultiplier tubes (or "PMT"), an avalanche photodiode (APD), etc., are also used to record light that mediated by, e.g., emitted by a label on, the particle. Flow cytometers may further include one or more electrical detectors. In certain embodiments, an electrical detector may be employed for detecting a disturbance caused by a particle passing through an electrical field propagated across an aperture in the path of the particles. Such flow cytometers having electrical detectors will contain a corresponding electrical energy emitting source that propagates an electrical field across the flow path or an aperture through which cells are directed. Any convenient electrical field and/or combination of fields with appropriate detector(s) may be used for the detection and/or measurement of particles passing through the field including but not limited to, e.g., a direct current electrical field, alternating current electrical field, a radio-frequency field, and the like.

Flow cytometers further include data acquisition, analysis and recording means, such as a computer, wherein multiple data channels record data from each detector for each cell as it passes through the sensing region. The purpose of the analysis system is to classify and count cells wherein each cell presents itself as a set of digitized parameter values and to accumulate data for the sample as a whole.

The flow cytometry can comprise a bead-based assay, such as a sandwich protocol for bead-based assay. In one embodiment, determining the level of cytokines/chemokines by flow cytometry comprises contacting the sample with beads comprising an antibodies that specifically bind to the cytokines/chemokines of interest, e.g., one bead for each cytokine/chemokine of interest, washing the beads and contacting the washed beads with fluorescently labeled secondary antibodies that specifically bind to cytokines/chemokines, e.g., one fluorescently labeled secondary antibody that for each cytokines/chemokine of interest, washing the beads and detecting the presence of bead bound fluorescently labeled secondary antibodies that specifically bind to the cytokines/chemokines of interest by detecting by flow cytometry the labels on the beads.

In a specific embodiment, determining the level of cytokines/chemokine of interest by flow cytometry comprises contacting the sample with a bead population made of beads comprising antibodies that specifically bind to two or more of, such as three or more of, including five or more of, e.g., ten or more of, including all of TNF-α, IL-4, IL-13, IL-2, GM-CSF, sCD40L, CCL5 (RANTES), CCL3 (MIP-1α), IL-6, IL-10, IFN-γ, VEGF, IL-8, and CCL4 (MIP-1β), washing the beads and contacting the washed beads with fluorescently labeled secondary antibodies, and detecting the presence of cytonkines/chemokines on the beads by detecting by flow cytometry the fluorescent labels on the beads. In some instances, the assay employed is BioLegend's LEGENDplex™ bead-based immunoassay (BioLegend, San Diego, Calif.).

The fluorescent label used to detect the bead can be selected from a large number of dyes that are commercially available from a variety of sources, such as Molecular Probes (Eugene, Oreg.) and Exciton (Dayton, Ohio). Examples of fluorophores of interest include, but are not limited to, 4-acetamido-4'-isothiocyanatostilbene-2,2'disulfonic acid; acridine and derivatives such as acridine, acridine orange, acridine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumarin 151); cyanine and derivatives such as cyanosine, Cy3, Cy5, Cy5.5, and Cy7; 4',6-diaminidino-2-phenylindole (DAPI); 5', 5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin; o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; or combinations thereof. Other fluorophores or combinations thereof known to those skilled in the art may also be used, for example those available from Molecular Probes (Eugene, Oreg.) and Exciton (Dayton, Ohio).

In certain embodiments, determining the level of cytokines/chemokines is performed by ELISA. ELISA can be direct ELISA, indirect ELISA, competitive ELISA, or sandwich ELISA. Various methods of conducting ELISA assay are known in the art and can be used in the methods disclosed herein.

The test sample employed in embodiments of the invention may vary, and can be obtained from useful organ or tissue. The organ or tissue can be brain, eyes, pineal gland, pituitary gland, thyroid gland, parathyroid glands, thorax, heart, lung, esophagus, thymus gland, pleura, adrenal glands, appendix, gall bladder, urinary bladder, large intestine, small intestine, kidneys, liver, pancreas, spleen, stoma, ovaries, uterus, or skin. The test sample can be a type of a body fluid. The body fluid can be aqueous humor, vitreous humor, bile, blood, cerebrospinal fluid, chyle, endolymph, perilymph, lymph, mucus, pericardial fluid, peritoneal fluid, pleural fluid, pus, rheum, saliva, sputum, synovial fluid, blood, serum or plasma.

In certain embodiments, the methods further include treating the subject for COVID-19 based on the assigned pathological type for the subject. The term "treatment" or "treating" as used herein refers to the ability to ameliorate, suppress, mitigate, or eliminate clinical symptoms of COVID-19. The effect may be prophylactic in terms of completely or partially preventing severe COVID-19 disease outcomes and/or may be therapeutic in terms of partially or completely suppressing COVID-19 symptoms. Treatments that may be employed include, but are not limited to: immune-based, e.g., immunosuppressive, immune-modulator, and antiviral therapies. As such in some instances, the methods include administering an immunosuppressive, immune-modulator or an antiviral therapy to the subject if the subject is assigned a long-COVID pathological type. In some instances, the methods include administering an immunosuppressive, immune-modulator or an antiviral therapy to the subject if the subject is assigned a sever-COVID pathological type.

In some instances, the treatment includes an immune-based therapy. Immune-based therapies may include agents that modulate the immune response. In some instances, the immune-based therapy comprises an antibody or fragment thereof. In some instances, the antibody or fragment thereof is specific to a coronaviral antigen, e.g., an antigen derived from SARS-CoV-2. In other instances, the antibody or fragment thereof is not specific to a coronaviral antigen. In some cases, the immune-based therapy includes convalescent plasma. In some embodiments, the immune-based therapy includes mesenchymal stem cells. In some cases, the immune-based therapy includes an immunomodulatory agent. The immunomodulatory agent may be selected from the group consisting of: a corticosteroid, an interferon, an interleukin-1 inhibitor, an interleukin-6 inhibitor, and a kinase inhibitor. Suitable corticosteroids include, e.g., dexamethasone, prednisone, methylprednisolone, and hydrocortisone. Suitable interferons include, e.g., interferon alpha and interferon beta. Suitable interleukin-1 inhibitors include, e.g., anakinra. Suitable interleukin-6 inhibitors include, e.g., anti-interleukin-6 receptor monoclonal antibodies such as, e.g., sarilumab and tocilizumab, and anti-interleukin-6 monoclonal antibodies such as, e.g., siltuximab. Suitable kinase inhibitors include, e.g., Bruton's tyrosine kinase inhibitors such as, e.g., Acalabrutinib, ibrutinib, Zanubrutinib, and Janus kinase inhibitors such as, e.g., Baricitinib, Ruxolitinib, Tofacitinib.

In some instances, the treatment includes an antiviral medication. The antiviral medication may include a small molecule. Naturally occurring or synthetic small molecule compounds of interest include numerous chemical classes, such as organic molecules, e.g., small organic compounds having a molecular weight of more than 50 and less than about 2,500 Daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols. Suitable antiviral medications may include, e.g., Remdesivir (veklury), chloroquine, hydroxychloroquine with or without azithromycin, ivermectin, an HIV protease inhibitor (e.g., lopinavir/ritonavir).

In some instances, the treatment includes an adjunctive therapy. In some cases, the adjunctive therapy includes an antithrombotic therapy including, e.g., an anticoagulant or antiplatelet therapy. In some cases, the adjunctive therapies include vitamin and mineral supplements such as, e.g., vitamin C, vitamin D, and zinc.

In some instances, treatment includes administering an active agent that inhibits CCR5 mediated CCL5 signaling, such as an inhibitor of CCR5/CCL5 binding interaction. Any convenient active agent may be employed in such embodiments, where active agents include, but are not limited to, CCR5 antagonists/inhibitors, CCL5 antagonists/inhibitors, etc. Furthermore, any convenient type of active agent may be employed, where examples of active agent types include, but are not limited to: small molecules, nucleic acids, specific binding member for CCR5 or CCL5, such as, but not limited to, antibodies, aptamers, peptides, etc.

In some instances, the active agent is a small molecule agent that exhibits the desired activity. Naturally occurring or synthetic small molecule compounds of interest include numerous chemical classes, such as organic molecules, e.g., small organic compounds having a molecular weight of more than 50 and less than about 2,500 Daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In some cases, the active agent is a protein or fragment thereof or a protein complex. In some cases, the active agent is an antibody binding agent or derivative thereof. The term "antibody binding agent" as used herein includes polyclonal or monoclonal antibodies or fragments, that are sufficient to bind to an analyte of interest, e.g., CCR5 or CCL5. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. In some cases, the active agent is an enzyme or enzyme complex. In some cases, the active includes a phosphorylating enzyme, e.g., a kinase. In some cases, the active is a complex including a guide RNA and a CRISPR effector protein, e.g., Cas9, used for targeted cleavage of a nucleic acid.

In some cases, the active agent is a nucleic acid. The nucleic acids may include DNA or RNA molecules. In certain embodiments, the nucleic acids modulate, e.g., inhibit or reduce, the activity of a gene or protein, e.g., by reducing or downregulating the expression of the gene. The nucleic acid may be a single stranded or double-stranded and may include modified or unmodified nucleotides or non-nucleotides or various mixtures and combinations thereof. In some cases, the active agent includes intracellular gene silencing molecules by way of RNA splicing and molecules that provide an antisense oligonucleotide effect or a RNA interference (RNAi) effect useful for inhibiting gene function. In some cases, gene silencing molecules, such as, e.g., antisense RNA, short temporary RNA (stRNA), double-stranded RNA (dsRNA), small interfering RNA (siRNA), short hairpin RNA (shRNA), microRNA (miRNA), tiny non-coding RNA (tncRNA), snRNA, snoRNA, and other RNAi-like small RNA constructs, may be used to target a protein-coding as well as non-protein-coding genes. In some case, the nucleic acids include aptamers (e.g., spiegelmers). In some cases, the nucleic acids include antisense compounds. In some cases, the nucleic acids include molecules which may be utilized in RNA interference (RNAi) such as double stranded RNA including small interfering RNA (siRNA), locked nucleic acid (LNA) inhibitors, peptide nucleic acid (PNA) inhibitors, etc.

As described above, in some instances the active agent employed in embodiments of methods of the invention is a CCR5 targeting agent, such as a CCR5 inhibitor/antagonist. CCR5 targeting agents are described in U.S. Patent Application Pub. Nos. 1 20180303830, 20170231991, 20140109245, and 20130303512; the disclosures of which are incorporated herein by reference in their entirety. Useful drugs targeting CCR5 may, in some instances, include CCR5 antagonists, such as but not limited to e.g., small molecule (including peptide and non-peptide small molecule) inhibitors, antibodies, and the like. Non-limiting examples of CCR5 antagonists include: Maraviroc (aka Selzentry or Celsentri), INCB-9471 ((4,6-dimethylpyrimidin-5-yl)-[4-[(3S)-4-[(1R,2R)-2-ethoxy-5-(trifluoromethyl)-2,3-dihydro-1H-inden-1-yl]-3-methylpiperazin-1-yl]-4-methylpiperidin-1-yl]methanone; orally available CCR5 antagonist; PubChem CID: 49871007), Leronlimab (PRO-140, a humanized monoclonal antibody directed against CCR5), Aplaviroc (4-(4-{[(3R)-1-butyl-3-[(R)-cyclohexyl(hydroxy)methyl]-2,5-dioxo-1,4,9-triazaspiro[5.5]undecan-9-yl]methyl}phenoxy)benzoic acid; a potent non-competitive allosteric antagonist of the CCR5 receptor), Vicriviroc (5-{4-[(3S)-4-[(1R)-2-methoxy-1-[4-(trifluoromethyl)-phenyl]ethyl]-3-methylpiperazin-1-yl]-4-methylpiperidine-1-carbonyl}-4,6-dimethylpyrimidine; CCR5 entry inhibitor previously named SCH 417690 and SCH-D), Cenicriviroc (S,E)-8-(4-(2-Butoxyethoxy)phenyl)-1-isobutyl-N-(4-(((1-propyl-1H-imidazol-5-yl)methyl)sulfinyl)phenyl)-1, 2,3,4-tetrahydrobenzo[b]azocine-5-carboxamide); OB-002 (Orion Biotechnologies); BMS-813160 (N-[(1R,2S,5R)-5-[(1,1-dimethylethyl)amino]-2-[(3S)-3-[[7-(1,1-dimethylethyl)pyrazolo[1,5-a]-1,3,5-triazin-4-yl]amino]-2-oxo-1-pyrrolidinyl]cyclohexyl]-acetamide); fully human monoclonal antibodies to CCR5 (such as the HGS004 as described by Lalezari et al., J Infect Dis. (2008) 197(5):721-7), and the like.

In some instances, the active agent is an antibody that binds to CCR5. An antibody that specifically binds to CCR5 can be polyclonal or monoclonal antibody or fragments that are sufficient to bind CCR5. The antibody fragments can be, for example, monomeric Fab fragments, monomeric Fab' fragments, or dimeric F(ab)'2 fragments, single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. An antibody that specifically binds to CCR5 can be a humanized monoclonal antibody, such as Leronlimab (PRO 40), PA14, 2D7, RoAb13, RoAb14, 45523. Certain examples of CCR5 antibodies are described by the reference Olson et al. *Curr Opin HIV AIDS*, 2009 March; 4(2):104-111, which is herein incorporated by reference in its entirety. In some instances, the active agent is Leronlimab. In some instances, the active agent is a small molecule inhibitor of CCR5, such as but not limited to: Maraviroc, vicriviroc, aplaviroc, SCH-C, BMS-813160; OB-002; Cenicriviroc or TAK-779.

Where desired, active agents may be administered to a subject as a pharmaceutical composition.

Where desired, active agents may be administered to a subject as a pharmaceutical composition. The active agent(s) may be administered to the adult mammal using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al., Anal Biochem. (1992) 205:365-368. The DNA may be coated onto gold microparticles, and delivered intradermally by a particle bombardment device, or "gene gun" as described in the literature (see, for example, Tang et al., Nature (1992) 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

In practicing embodiments of the invention, active agent compositions may be administered according to any desired dosage, such as once per day, a few or several times per day, or even multiple times per day, depending upon, among other things, the indication being treated and the judgment of the prescribing physician. For example, in some instances, compositions that include one or more active agents may be administered once per day, a few or several times per day, or even multiple times per day, depending upon, among other things, the indication being treated and the judgment of the prescribing physician.

Depending on whether systemic and/or local treatment is chosen, methods of administration may be chosen depending also on the condition being treated and the pharmaceutical composition being administered. Administration of an effective amount (in one or multiple doses) of the subject agent(s) can be done in a variety of ways, including, but not limited to, subcutaneously, intravenously, intraperitoneally, intramuscularly, and direct injection to specified organs or tissues, systemic administration, etc. Administration of the pharmaceutical compositions may be through a single route or concurrently by several routes. As such, the active agent can be administered to a subject via a suitable route of administration and include oral, mucosal (e.g., nasal, sublingual, vaginal, buccal, or rectal), parenteral (e.g., subcutaneous, intravenous, bolus injection, intramuscular, or intra-arterial, intraperitoneal), or transdermal.

In those embodiments where an effective amount of an active agent is administered to the adult mammal, the amount or dosage is effective when administered for a suitable period of time so as to evidence a reduction in one or more symptoms of the target disease. In some instances, an effective amount or dose of active agent will not only slow or halt the progression of the disease condition but will also induce the reversal of the condition, i.e., will cause an improvement in the subject's condition. Where desired, effectiveness of treatment may be assessed using any convenient protocol. Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, one or more target symptoms of the disease condition.

In some instances, the methods include assessing treatment efficacy by determining whether the subject maintains the long-COVID pathological type. For example, during treatment of a subject having a long-COVID pathological type, embodiments of the methods may include further assessing the subject in accordance with the methods to determine efficacy of the treatment. For example, a subject may be assessed in accordance with embodiments of the invention one or more times following treatment to determine whether the subject should still be assigned as having the long-COVID pathological type, or whether subject no longer has the long-COVID pathological type. In such an embodiment, the subject may be assessed to determine whether the subject still has a long-COVID pathological score, e.g., S1 described above. The determination of the pathological type or absence thereof may be employed as a measure or evaluation of the therapeutic treatment regimen being administered to the subject. In such embodiments, the frequency of assaying may vary, such as daily, every two days, weekly, every two weeks, etc.

In some instances, the methods include determining when to administer therapy to the subject if the subject is assigned a severe-COVID pathological type. The methods described can also be used to determine the appropriate time to discontinue therapy or change therapy in the instance that the severity or long scores have not changed after therapy.

Methods of Treating Chronic COVID-19

Also provide are methods of treating a subject for chronic COVID-19 (which may also be referred to as chronic COVID-19 syndrome). Subject suffering from chronic COVID-19 may be referred to as long haulers, and may suffer from one or more symptoms indicative of chronic COVID-19. "Long Haulers" and subjects who experience a multitude of symptoms from several weeks to months after recovering from their acute illness and presumably months after viral clearance. These symptoms include joint pain, muscle aches, fatigue, "brain fog" and others. These symptoms can commonly resemble rheumatic diseases such as rheumatoid arthritis, autoimmune disorders, and others such as fibromyalgia and chronic fatigue syndrome (Chen et al., "Inflammatory responses and inflammation-associated diseases in organs", Oncotarget 9, 7204-7218 (2018)). Many of these common disorders are caused by inflammation, hyper- and/or auto-immunity and some such as chronic fatigue are associated with viral persistence after an acute infection with pathogens such as Epstein Barr and Cytomegalovirus (Rasa et al., "Chronic viral infections in myalgic encephalomyelitis/chronic fatigue syndrome (ME/CFS)", J Transl Med 16, 268 (2018)). Recent studies including those from our laboratory have suggested that (CC) may be caused by persistent COVID itself (Mudd et al., "SARS-CoV-2 viral RNA shedding for more than 87 days in an individual with an impaired CD8+ T-cell response", Front Immunol (in press)). In embodiments of these methods, the subject may have been identified as long haulers using the methods of assigning a COVID pathological type for a subject suffering from COVID-19 of the invention, e.g., as described above. Since "long haulers" clearly represent an immunologically distinct patient (FIG. 4B) from active COVID-19, it would not be obvious that treatments that ameliorate the immunologic abnormalities in active COVID would necessarily be effective in "long haulers".

The terms "subject," "individual," "host," and "patient," are used interchangeably herein and refer to any mammalian subject for whom diagnosis, treatment, or therapy is desired, particularly humans. As reviewed above, by "treatment" it is meant that at least an amelioration of one or more symptoms associated with chronic COVID-19 afflicting the subject is achieved, where amelioration is used in a broad sense to refer to at least a reduction in the magnitude of a parameter, e.g., a symptom, associated with the impairment being treated. As such, treatment also includes situations where chronic COVID-10, or at least symptoms associated therewith, is completely inhibited, e.g., prevented from happening, or stopped, e.g., terminated, such that the adult mammal no longer suffers from the impairment, or at least the symptoms that characterize the impairment.

In embodiments of such methods, aspects include administering to the subject (which may be a long hauler subject) a CCR5/CCL5 interaction inhibitor to treat the subject for chronic COVID-19, e.g., given the expression of CCR5 on the aforementioned antigen presenting cells (CD14Lo, CD16+). In some instances, treatment includes administering an active agent that inhibits CCR5 mediated CCL5 signaling, such as an inhibitor of CCR5/CCL5 binding interaction. Any convenient active agent may be employed in such embodiments, where active agents include, but are not limited to, CCR5 antagonists/inhibitors, CCL5 antagonists/inhibitors, etc. Furthermore, any convenient type of active agent may be employed, where examples of active agent types include, but are not limited to: small molecules, nucleic acids, specific binding member for CCR5 or CCL5, such as, but not limited to, antibodies, aptamers, peptides, etc. In some instances, the active agent is a small molecule agent that exhibits the desired activity. Naturally occurring or synthetic small molecule compounds of interest include numerous chemical classes, such as organic molecules, e.g., small organic compounds having a molecular weight of more than 50 and less than about 2,500 Daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below. Examples of small molecule active agents of interest include, but are not limited to small molecule CCR5 antagonists, such as but not limited to e.g., small molecule (including peptide and non-peptide small molecule) inhibitors, antibodies, and the like. Non-limiting examples of such CCR5 antagonists include: Maraviroc (aka Selzentry or Celsentri), INCB-9471 ((4,6-dimethylpyrimidin-5-yl)-[4-[(3S)-4-[(1R,2R)-2-ethoxy-5-(trifluoromethyl)-2,3-dihydro-1H-inden-1-yl]-3-methylpiperazin-1-yl]-4-methylpiperidin-1-yl]methanone; orally available CCR5 antagonist; PubChem CID: 49871007), Aplaviroc (4-(4-{[(3R)-1-butyl-3-[(R)-cyclohexyl(hydroxy)methyl]-2,5-dioxo-1,4,9-triazaspiro[5.5]undecan-9-yl]methyl}phenoxy)benzoic acid; a potent noncompetitive allosteric antagonist of the CCR5 receptor); Vicriviroc (5-{4-[(3S)-4-[(1R)-2-methoxy-1-[4-(trifluoromethyl)-phenyl]ethyl]-3-methylpiperazin-1-yl]-4-methylpiperidine-1-carbonyl}-4,6-dimethylpyrimidine; CCR5 entry inhibitor previously named SCH 417690 and SCH-D); Cenicriviroc (S,E)-8-(4-(2-Butoxyethoxy)phenyl)-1-isobutyl-N-(4-(((1-propyl-1H-imidazol-5-yl)methyl)sulfinyl)phenyl)-1,2,3,4-tetrahydrobenzo[b]azocine-5-carboxamide); OB-002 (Orion Biotechnologies); BMS-813160 (N-[(1R,2S,5R)-5-[(1,1-dimethylethyl)amino]-2-[(3S)-3-[[7-(1,1-dimethylethyl)pyrazolo[1,5-a]-1,3,5-triazin-4-yl]amino]-2-oxo-1-pyrrolidinyl] cyclohexyl]-acetamide); and the like. In some instances, the active agent is a small molecule inhibitor of CCR5, such as but not limited to: Maraviroc, vicriviroc, aplaviroc, SCH-C, BMS-813160; OB-002; Cenicriviroc or TAK-779.

In some cases, the active agent is a protein or fragment thereof or a protein complex. In some cases, the active agent is an antibody binding agent or derivative thereof. The term "antibody binding agent" as used herein includes polyclonal or monoclonal antibodies or fragments, that are sufficient to bind to an analyte of interest, e.g., CCR5 or CCL5. The antibody fragments can be, for example, monomeric Fab fragments, monomeric Fab' fragments, or dimeric F(ab)'2 fragments. Also within the scope of the term "antibody binding agent" are molecules produced by antibody engineering, such as single-chain antibody molecules (scFv) or humanized or chimeric antibodies produced from monoclonal antibodies by replacement of the constant regions of the heavy and light chains to produce chimeric antibodies or replacement of both the constant regions and the framework portions of the variable regions to produce humanized antibodies. An antibody that specifically binds to CCR5 can be a humanized monoclonal antibody, such as Leronlimab (PRO 40), PA14, 2D7, RoAb13, RoAb14, 45523. Certain examples of CCR5 antibodies are described by the reference Olson et al. *Curr Opin HIV AIDS*, 2009 March; 4(2):104-111, which is herein incorporated by reference in its entirety. Fully human monoclonal antibodies to CCR5 also include HGS004 (e.g., as described by Lalezari et al., J Infect Dis. (2008) 197(5):721-7), and the like.

In some cases, the active agent is a nucleic acid. The nucleic acids may include DNA or RNA molecules. In certain embodiments, the nucleic acids modulate, e.g., inhibit or reduce, the activity of a gene or protein, e.g., by reducing or downregulating the expression of the gene. The nucleic acid may be a single stranded or double-stranded and may include modified or unmodified nucleotides or non-nucleotides or various mixtures and combinations thereof. In some cases, the active agent includes intracellular gene silencing molecules by way of RNA splicing and molecules that provide an antisense oligonucleotide effect or a RNA interference (RNAi) effect useful for inhibiting gene function. In some cases, gene silencing molecules, such as, e.g., antisense RNA, short temporary RNA (stRNA), double-stranded RNA (dsRNA), small interfering RNA (siRNA), short hairpin RNA (shRNA), microRNA (miRNA), tiny non-coding RNA (tncRNA), snRNA, snoRNA, and other RNAi-like small RNA constructs, may be used to target a protein-coding as well as non-protein-coding genes. In some case, the nucleic acids include aptamers (e.g., spiegelmers). In some cases, the nucleic acids include antisense compounds. In some cases, the nucleic acids include molecules which may be utilized in RNA interference (RNAi) such as double stranded RNA including small interfering RNA (siRNA), locked nucleic acid (LNA) inhibitors, peptide nucleic acid (PNA) inhibitors, etc.

As described above, in some instances the active agent employed in embodiments of methods of the invention is a CCR5 targeting agent, such as a CCR5 inhibitor/antagonist. CCR5 targeting agents are described in U.S. Patent Application Pub. Nos. 1 20180303830, 20170231991, 20140109245, and 20130303512; the disclosures of which are incorporated herein by reference in their entirety.

Where desired, active agents may be administered to a subject as a pharmaceutical composition. The active agent(s) may be administered to the adult mammal using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al., Anal Biochem. (1992) 205:365-368. The DNA may be coated onto gold microparticles, and delivered intradermally by a particle bombardment device, or "gene gun" as described in the literature (see, for example, Tang et al., Nature (1992) 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

In practicing embodiments of the invention, active agent compositions may be administered according to any desired dosage, such as once per day, a few or several times per day, or even multiple times per day, depending upon, among other things, the indication being treated and the judgment of the prescribing physician. For example, in some instances, compositions that include one or more active agents may be administered once per day, a few or several times per day, or even multiple times per day, depending upon, among other things, the indication being treated and the judgment of the prescribing physician.

Depending on whether systemic and/or local treatment is chosen, methods of administration may be chosen depending also on the condition being treated and the pharmaceutical composition being administered. Administration of an effective amount (in one or multiple doses) of the subject agent(s) can be done in a variety of ways, including, but not limited to, subcutaneously, intravenously, intraperitoneally, intramuscularly, and direct injection to specified organs or tissues, systemic administration, etc. Administration of the pharmaceutical compositions may be through a single route or concurrently by several routes. As such, the active agent can be administered to a subject via a suitable route of administration and include oral, mucosal (e.g., nasal, sublingual, vaginal, buccal, or rectal), parenteral (e.g., subcutaneous, intravenous, bolus injection, intramuscular, or intra-arterial, intraperitoneal), or transdermal.

In those embodiments where an effective amount of an active agent is administered to the adult mammal, the amount or dosage is effective when administered for a suitable period of time so as to evidence a reduction in one or more symptoms of the target disease. In some instances, an effective amount or dose of active agent will not only slow or halt the progression of the disease condition but will also induce the reversal of the condition, i.e., will cause an improvement the subject's condition. Where desired, effectiveness of treatment may be assessed using any convenient protocol. Biochemically, by an "effective amount" or "effective dose" of active agent is meant an amount of active agent that will inhibit, antagonize, decrease, reduce, or suppress by about 20% or more, e.g., by 30% or more, by 40% or more, or by 50% or more, in some instances by 60% or more, by 70% or more, by 80% or more, or by 90% or more, in some cases by about 100%, i.e., to negligible amounts, and in some instances reverse, one or more target symptoms of the disease condition.

In some instances, the methods include assessing treatment efficacy by determining whether the subject maintains the long-COVID pathological type. For example, during treatment of a subject having a long-COVID pathological type, embodiments of the methods may include further assessing the subject in accordance with the methods to determine efficacy of the treatment. For example, a subject may be assessed in accordance with embodiments of the invention one or more times following treatment to determine whether the subject should still be assigned as having the long-COVID pathological type, or whether subject no longer has the long-COVID pathological type. In such an embodiment, the subject may be assessed to determine whether the subject still has a long-COVID pathological score, e.g., S1 described above. The determination of the pathological type or absence thereof may be employed as a measure or evaluation of the therapeutic treatment regimen being administered to the subject. In such embodiments, the frequency of assaying may vary, such as daily, every two days, weekly, every two weeks, etc.

In some instances, the methods include determining when to administer therapy to the subject if the subject is assigned a severe-COVID pathological type. The methods described can also be used to determine the appropriate time to discontinue therapy or change therapy in the instance that the severity or long scores have not changed after therapy.

Kits

Also provided are kits that include reagents for quantitative, multiplex cytokine/chemokine panel in a test sample, e.g., as described above. As such, kits may include, in some instances, binding members, e.g., labeled, bead-bound, etc., for one or more cytokines/chemokines, e.g., as described above. A given kit may include labeled binding members specific for two or more of, such as three or more of, including five or more of, e.g., ten or more of, including all of TNF-α, IL-4, IL-13, IL-2, GM-CSF, sCD40L, CCL5 (RANTES), CCL3 (MIP-1α), IL-6, IL-10, IFN-γ, VEGF, IL-8, and CCL4 (MIP-1β), other assay reagents, e.g., flow cytometry reagents, ELISA reagents, etc. The kit components may be present in packaging, which packaging may be sterile, as desired.

Also present in the kit may be instructions for using the kit components. The instructions may be recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or sub-packaging) etc. In other embodiments, the instructions are present as an electronic storage data file present on a suitable computer readable storage medium, e.g., portable flash drive, DVD- or CD-ROM, etc. The instructions may take any form, including complete instructions for how to use the device or as a website address with which instructions posted on the world wide web may be accessed.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

I. ABSTRACT

A. Background: Individuals with systemic symptoms long after COVID-19 has cleared represent approximately ~10% of all COVID-19 infected individuals. Here we present a bioinformatics approach to predict and model the phases of COVID so that effective treatment strategies can be devised and monitored.

B. Methods: We investigated 164 individuals including normal individuals and patients spanning the COVID-19 disease continuum. We collected plasma and isolated PBMCs from 40 normal individuals, 30 individuals with mild-moderate COVID-19, 30 individuals with severe COVID-19, and 64 individuals with Chronic COVID-19 symptoms. Immune subset profiling and a 14-plex cytokine panel were run on all patients. Data was analyzed using machine learning methods to predict and distinguish the groups from each other.

C. Results: Using a multi-class deep neural network classifier to better fit our prediction model, we recapitulated a 100% precision, 100% recall and F1 score of 1 on the test set. Moreover, a first score specific for the chronic COVID-19 patients was defined as S1=(IFN-gamma+IL-2)/CCL4-MIP-1β. Second, a score specific for the severe COVID-19 patients was defined as S2=(10*IL-10+IL-6)−(IL-2+IL-8).

D. Conclusions: Severe cases are characterized by excessive inflammation and dysregulated T cell activation, recruitment, and counteracting activities. While chronic patients are characterized by a profile able to induce the activation of effector T cells with pro-inflammatory properties and the capacity of generating an effective immune response to eliminate the virus but without the proper recruitment signals to attract activated T cells.

II. MATERIAL/METHODS

A. Patients

Following informed consent, whole blood was collected in a 10 mL EDTA tube and a 10 mL plasma preparation tube (PPT). A total of 164 individuals were enrolled in the study consisting of 40 normal individuals, 30 mild-moderate COVID-19 patients, 30 severe COVID-19 patients and 64 chronic COVID (long hauler-LH) individuals. Long Haulers symptoms are listed in FIG. 1. Study subjects were stratified according to the following criteria.

Mild
1. Fever, cough, sore throat, malaise, headache, myalgia, nausea, diarrhea, loss of taste and small
2. No sign of pneumonia on chest imaging (CXR or CT Chest)
3. No shortness of breath or dyspnea Moderate:
1. Radiological findings of pneumonia fever and respiratory symptoms
2. Saturation of oxygen (SpO2)≥94% on room air at sea level Severe
1. Saturation of oxygen $(SpO_2)$<94% on room air at sea level
2. Arterial partial pressure of oxygen (PaO2)/fraction of inspired oxygen (FiO2)<300 mmHG
3. Lung infiltrate>50% within 24 to 48 hours
4. HR≥125 bpm
5. Respiratory rate 30 breaths per minute Critical
1. Respiratory failure and requiring mechanical ventilation, ECMO, high-flow nasal cannula oxygen supplementation, noninvasive positive pressure ventilation (BiPAP, CPAP)
2. Septic Shock-Systolic blood pressure<90 mmHg or Diastolic blood pressure<60 mmHg or requiring vasopressors (levophed, vasopressin, epinephrine
3. Multiple organ dysfunction (cardiac, hepatic, renal, CNS, thrombotic disease)

Post-Acute COVID-19 (Long COVID)
1. Extending beyond 3 weeks from the initial onset of first symptoms Chronic COVID-19
1. Extending beyond 12 weeks from the initial onset of first symptoms (Table 1)

B. High Parameter Immune Profiling/Flow Cytometry

Peripheral blood mononuclear cells were isolated from peripheral blood using LYMPHOPREP™ density gradient (STEMCELL Technologies, Vancouver, Canada). Aliquots 200 of cells were frozen in media that contained 90% fetal bovine serum (HyClone, Logan, Utah) and 10% dimethyl sulfoxide (Sigma-Aldrich, St. Louis, Mo.) and stored at −70° C. Cells were stained and analyzed as previously described (4) (Patterson) using a 17-color antibody cocktail.

C. Multiplex Cytokine Quantification

Fresh plasma was used for cytokine quantification using a customized 14-plex bead based flow cytometric assay (IncellKINE, IncellDx, Inc) on a CytoFlex flow cytometer as previously described using the following analytes: 'TNF-α', 'IL-4', 'IL-13', 'IL-2', 'GM-CSF', 'sCD40L', 'CCL5 (RANTES)', 'CCL3 (MIP-1α)', 'IL-6', 'IL-10', 'IFN-γ', 'VEGF', 'IL-8', and 'CCL4 (MIP-1β)' (Patterson et al., "CCR5 inhibition in Critical COVID-19 Patients Decreases Inflammatory Cytokines, Increases CD8 T-Cells, and Decreases SARS-CoV2 RNA in Plasma by Day 14", Int J Infect Dis (2020) doi: 10.1016/j.ijid.2020.10.101). For each patient sample, 25 μL of plasma was used in each well of a 96-well plate. Standard curves with serial 6-point dilutions of antigen were run on each plate for each cytokine. Raw data was analyzed using LegendPlex software (Biolegend, Inc San Diego Calif.). Samples were run in duplicate.

C. Data Processing

Data was imported and processed using Python 2.7, using the pandas library (version 1.1.0). and the numeric python module, numpy version 1.18.5. Our data consisted of 144 instances representing 4 classes (Normal-n=29, Mild-Moderate-n=26, Severe-n=25, Long Hauler-n=64). Each class had 14 columns, representing the different cytokine/chemokine analytes. Each analyte had different measurements which required a normalization process to reduce outlier effect and to facilitate algorithm convergence.

Normalization was done using Min-Max and based on a linear transformation of the original data. Min-Max maintains the original relationship between the data, while fitting it within a pre-defined boundary. The Python implementation of min-max calculates the range in such a manner that the range of the features will be defined between 0 and 1. For this reason, min-max normalization is also referred to as 0-1 normalization (or scaling). The typical min-max transformation is given in equation 1:

$$X = \frac{(X - X\min)}{X\max - X\min} \quad [1]$$

D. Target Variable Processing

Since Min-max normalization can only be applied to numeric variables a new variable defined as targets was created. The variable targets represent the different classes (Long Hauler, Severe, Mild-Moderate, and Normal) for the instances in the dataset. The resulting array has 4 classes for each state. The goal of our analysis is to properly identify/discriminate the instances that belong to the Severe state or the Long-Hauler state compared to other states. This goal can be achieved by building either binary classifiers for the Severe class and for the Long Hauler class, a multi-class predictor. For the construction of both models, t is required to separate the targets to reflect the dosing question: can a predictor discriminate between the Severe, Long Hauler and Other Sates.

To build the models that answer this question, we grouped the M-M and Normal labels in a new class which was distinct form the Severe and Long-Hauler states. We then proceeded to apply filters based on the task (binary or multi-class classification). For the Severe binary predictor, we conditioned the targets to be exactly Severe or else they were assigned to Not-Severe. This same task was done for Long-Haulers, were either an instance label was exactly labelled Long-Hauler or else it would be assigned to the Non-Long Hauler class. The multi-class predictor processing only requires to define three classes: Severe, Long-Hauler and Non-Severe-Non-Long-Hauler which was composed of the Normal and Mild-Moderate cases.

E. One-Hot Encoding of Targets

The implementation of one-hot encoding on the target variable, is based on the notion that multiple machine learning algorithms are unable to properly process categorical data. It is possible to use numeric replacements, such as integer values, but this can only be useful if there is an ordinal relationship within the variable. Such use would imply that there exists a vectorial relationship between the labels, for example, in our classes we have Normal, Mild-Moderate, Severe and Long-Haulers. If we assigned a vector of integers from 0 to 4 in their corresponding orders to the classes, it would assume the presence of a vectorial distance between Normal and Long Hauler or V0->V4.

To properly design an experiment that reflects the above, we used one-hot encoding. After applying one-hot encoding, the labels are substituted with 1 and 0, where 1 represents the presence of the class and 0 the absence. The use of one-hot encoding corrects for the vector-distance assumption of integer or categorical classes, where higher or larger values could be interpreted as better.

Definition of Precision, Recall and F1 Score (Supplementary)

The precision (equation 2) is a measure of the percentage of the results that are relevant. The metric Recall measures the percentage of the total relevant results that are correctly classified by the predictor (equation 3). The harmonic mean between these two measures is known as the F1 score and ranges from 0 to 1, the closer to is to 1, the better the model performs (equation 4). The F1 score for both false positives (FP) and false negatives (FN) as well as for true positives (TP).

$$\text{Precision} = \frac{TruePositive}{TruePositive + FalsePositive} \quad [2]$$

$$\text{Recall} = \frac{TruePositive}{TruePositive + FalseNegative} \quad [3]$$

$$F1 = \frac{2 * \text{Precision} * \text{Recall}}{\text{Precision} + \text{Recall}} = \frac{TP}{TP + 1/2(FP + FN)} \quad [4]$$

F. Feature Selection and Classification Using Random Forest

Data pre-processing, target variable processing and the encoding of targets were performed before classification as above. Feature selection is the process of reducing dimensionality of the dataset by selecting those features or variables that are more informative than those that are not.

To perform feature selection, we implemented the RandomForestClassifier method from Sci-kit Learn. Random Forest allows for identification of features that better separate the classes by determining what percentage of the nodes that use those features have a reduction in entropy or impurity (which are measures of how well separated the instances are using a feature).

The binary classifier was constructed using the data points and their features with the one-hot encoded target corresponding to: 1) the severe and non-severe model, 2) the long hauler and non-long hauler model and 3) the multiclass model. The model was built with the RandomForestClassifier method from Sci-kit Learn, with the number of trees constructed set to 750, the number of features set as the square root of the feature space, and the node depth equal to 4 to avoid overfitting. These parameters were set for binary and multi-class predictors. Model performance was measured using: precision, recall and the F1 score (see supplementary information).

of T-cell exhaustion (co-expression of PD-1, LAG3, and or CTLA-4). B-cells were significantly elevated compared to normal individuals (P<0.001) as was the CD14+, CD16+ monocytic subset (P<0.001) (Table 1).

TABLE 1

Immunologic parameters of study participants

| Average | CD3 + % | CD4% | CD8% | CD4 + PD1 + % | CD4 + LAG3 + % | CD4 + CTLA4 + % | CD4 + FoxP3 + % |
|---|---|---|---|---|---|---|---|
| Normals | 64.45 | 53.89 | 33.83 | 35.62 | 0.94 | 1.51 | 6.21 |
| Lower CI | 54.39 | 43.21 | 27.20 | 28.36 | 0.49 | 0.75 | 4.54 |
| Upper CI | 74.50 | 64.57 | 40.46 | 42.89 | 1.39 | 2.26 | 7.87 |
| Long Hauler | 48.98 | 56.18 | 35.36 | 17.78 | 0.72 | 4.06 | 2.58 |

| Average | CD8 + PD1 + % | CD8 + LAG3 + % | CD8 + CTLA4 + % | CD19 + % | CD14 + CD16 − % | CD16 + CD14 + % | CD16 + CD14 − % |
|---|---|---|---|---|---|---|---|
| Normals | 43.76 | 4.35 | 1.39 | 6.04 | 42.79 | 9.00 | 32.68 |
| Lower CI | 33.50 | 2.71 | 0.74 | 5.04 | 34.41 | 4.60 | 25.49 |
| Upper CI | 54.01 | 5.99 | 2.03 | 7.04 | 51.16 | 13.41 | 39.86 |
| Long Hauler | 31.99 | 0.71 | 3.11 | 13.14 | 19.07 | 29.30 | 33.86 |

| Average (pg/ml) | TNF-α | IL-4 | IL-13 | IL-2 | GM-CSF | sCD40L | CCL5 (RANTES) |
|---|---|---|---|---|---|---|---|
| Normals | 9.09 | 4.18 | 3.94 | 6.17 | 51.27 | 7192.39 | 10781.84 |
| Lower CI | 7.37 | 2.17 | 1.79 | 5.53 | 25.72 | 5148.85 | 9764.99 |
| Upper CI | 10.81 | 6.18 | 6.09 | 6.82 | 76.82 | 9235.92 | 11798.68 |
| Long Haulers | 7.72 | 17.03 | 4.21 | 16.16 | 12.46 | 18302.41 | 12505.06 |
| Mild-Mod | 6.82 | 2.33 | 2.40 | 5.90 | 56.13 | 10673.72 | 11627.70 |
| Severe | 5.39 | 2.39 | 2.26 | 5.43 | 20.31 | 12306.39 | 11581.47 |

| Average (pg/ml) | CCL3 (MIP-1α) | IL-6 | IL-10 | IFN-γ | VEGF | IL-8 | CCL4 (MIP-1β) |
|---|---|---|---|---|---|---|---|
| Normals | 22.82 | 2.21 | 0.67 | 1.94 | 9.32 | 16.87 | 76.84 |
| Lower CI | 13.05 | 1.65 | 0.42 | 0.63 | 6.36 | 13.03 | 61.00 |
| Upper CI | 32.60 | 2.77 | 0.92 | 3.26 | 12.28 | 20.72 | 92.67 |
| Long Haulers | 97.81 | 20.47 | 12.23 | 86.60 | 41.03 | 35.98 | 35.10 |
| Mild-Mod | 18.75 | 8.74 | 0.63 | 1.15 | 17.39 | 17.37 | 94.40 |
| Severe | 16.54 | 144.15 | 3.10 | 2.06 | 25.52 | 10.87 | 64.84 |

G. Predictor Construction Using Deep Neural Networks

The deep neural network (DNN) binary and multiclass classifiers were constructed with a basic DNN architecture built on stacks of perceptrons, where each subsequent layer is connected to the previous one. Each layer transformed the inputs using the rectified linear activation function or ReLU. The DNN models were constructed to have 1 input layer, 3 hidden layers with 10 neurons each, followed by layer with 6 neurons. Finally, the output layer consists of 3 neurons, for the outputs (classes) and the softmax (multi-class) or sigmoid (binary) function.

In order for a DNN to generate the best possible predictions, we minimized the loss function or error of the model using the ADAM optimizer to search for the optimal combination of hyperparameters. When setting the optimizer, we defined the learning rate to 1e-3. The loss function was set to categorical cross entropy because the targets are one-hot encoded.

III. RESULTS

A. Immune Profiling

To determine if immunologic abnormalities remain in Long Haulers, we performed high parameter immune cell quantification and characterization in a subset of individuals with preserved peripheral blood mononuclear cells. We determined B-cells, T-cells, and monocytes including subsets and including CD4/CD8 activation and exhaustion. Unlike active COVID-19, the CD4 and CD8 T-cell populations were within normal limits and there was no evidence Interestingly, these two immune cell populations have been shown to be chronically infected by different viruses. B-cells by Epstein-Barr and the CD14+, CD16+ monocytic subset by HIV-1 and by HCV (Coquillard & Patterson, "HCV-Infected, Monocyte Lineage Reservoirs Differ in Individuals with or without HIV Co-Infection", J Infect Dis 2009; 200:947-954).

To further characterize the immune response in Long Haulers, we performed quantitative, multiplex cytokine/chemokine panel on 30 normal individuals to establish the normal range of the assay. We then analyzed 64 long haulers and compared the cytokine/chemokine profile (Table 1). IL-2, IL-4, CCL3, IL-6, IL-10, IFN-γ, and VEGF were all significantly elevated compared to normal control (all P<0.001). Conversely GM-CSF and CCL4 were significantly lower than normal controls. Further exacerbating this hyper-immunity was the significant decrease in T regulatory cells compared to normal individuals (P<0.001).

B. Random Forest Binary and Multi-Class Models for Feature Selection and Prediction We separated the dataset into a training and test split of 90% training and 10% test. This proportion was used because of the reduced number of instances in the dataset. Also, to ensure reproducible results we set the same random seed for all the models.

The first model we constructed was the multi-class predictor. This model attempted to separate the severe, long hauler and non-severe-non-long hauler class. This classifier achieved 97% precision, 97% recall and a F1 score of 0.97 in the training partition. In the test split, it performed slightly better, with a precision of 100%, a recall of 100% and thus and F1 score of 1.00 (Table 2).

TABLE 2

Performance Metrics for the Random Forest Classifiers in the test split.

| Model | Precision % | Recall % | F1 Score |
|---|---|---|---|
| Long Hauler-Full Features | 100 | 100 | 1.00 |
| Severe- Full Features | 100 | 100 | 1.00 |
| Multi-Class-Full Features | 100 | 100 | 1.00 |

This model was then analyzed to identify the most relevant or informative features. This resulted in the identification of 6 features with an importance score above the importance median (0.063895) and average (0.07143). The identified features were: IFN-gamma, IL-2, IL-6, IL-10, IL-8, CCL4-MIP-1β, in importance order. The full list of ranked features can be seen in FIG. 2.

Regarding the long hauler and non-long hauler binary classifier, our results were consistent between the training and the test set. In both partitions the precision and the recall were 100% (1.00) and thus the F1 score equaled 1.00. The observation that the model had good metrics in the test split when compared to the train set is a valuable indicator that the model is not overfitting, and that it is capable of generalizing the patters identified in the training data. The overview of the precision, recall and F1 score for the binary long hauler model can be seen in Table 2. Feature importance analysis of the binary model, revealed that the features identified as important for this model were the same features identified as important for the multi-class predictor. This finding suggests there is an important group of characteristics or variables that are influential in the identification of long hauler data points from other instances. These features can be seen in FIG. 2.

Figure 2:
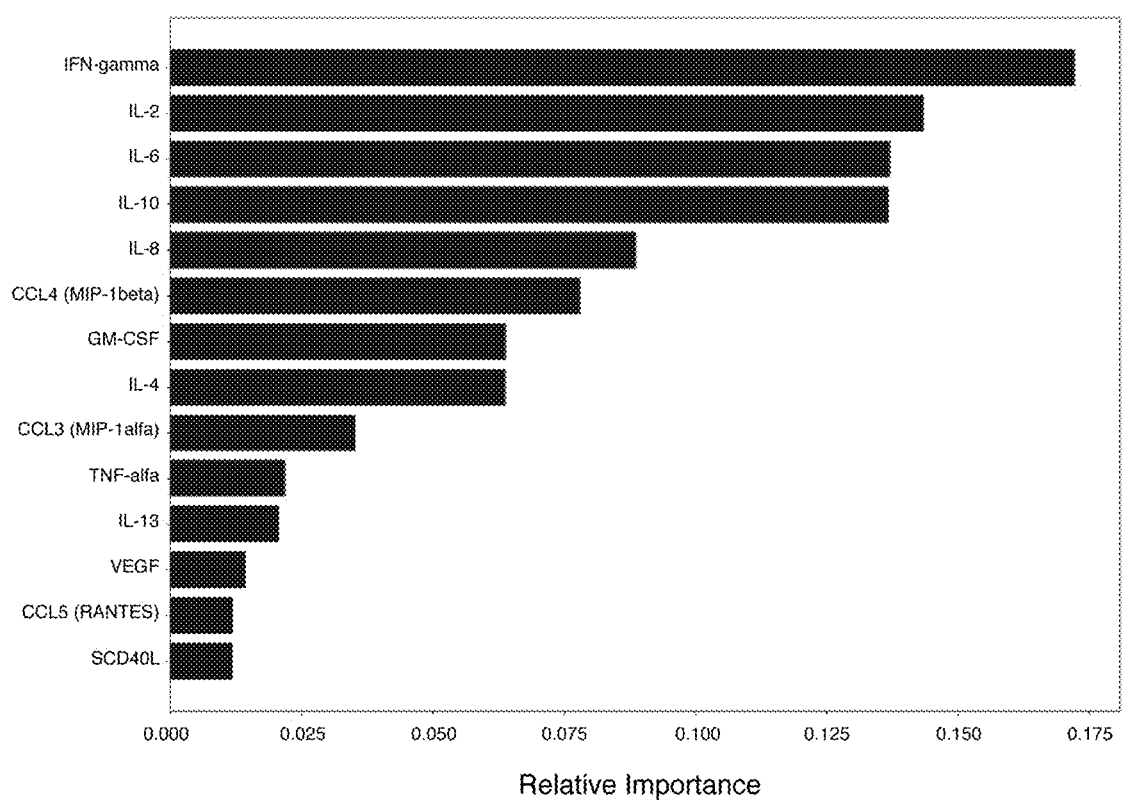
FIG. 2 graphically illustrates feature importance for multi-class classifier using Random Forest predictor.

The severe binary model, which classified instances between non-severe and severe resulted in high performance metrics for both the training and test splits. As shown in Table 2, the performance of this model was an indicator of no potential overfitting. This model is of special interest given the small number of instances in the severe class. Furthermore, the feature importance analysis of this model revealed that the relevant features were also the same as with the multi-class model and with the long hauler binary classifier (FIG. 2). This finding reinforces our notion that these group of relevant features could impact classification, or that could have some biological significance worth exploring by means of other analysis like a separation heuristic.

C. Deep Neural Network Binary Classifiers Using the Full Feature Set

The deep neural network (DNN) classifier was constructed layers of neurons. Each layer transformed the inputs using the rectified linear activation function or ReLU. The DNN model was constructed to have 1 input layer, 3 hidden layers with 10 neurons each, followed by layer with 6 neurons. Finally, the output layer consists of 3 neuros, for the outputs (classes) and the softmax (multi-class) or sigmoid (binary) function. This architecture was used for the multi-class model and the binary models.

The results of the long hauler binary models, revealed differences of ~5% between the metrics of the training and the test set (Table 3).

TABLE 3

Performance Metrics of the DNN full feature model in the training and test splits

| DNN | Precision % | Recall % | F1 Score |
|---|---|---|---|
| Multi-Class - Full Features -Train | 99 | 97 | 0.98 |
| Long Hauler - Full Features -Train | 100 | 100 | 1.00 |
| Severe - Full Features - Train | 98 | 100 | 0.99 |
| Multi-Class - Full Features -Test | 100 | 100 | 1.00 |
| Long Hauler - Full Features -Test | 94 | 94 | 0.93 |
| Severe - Full Features - Test | 75 | 92 | 0.79 |

Such difference is not significant to attribute overfitting to the training set. In contrast, the severe binary model had significant differences between the performance metrics of the training and the test set (Table 3). This is evident in the precision score, with 98% in the training set and 75% on the test set, and thus the F1 score with a difference of 20% (0.99 on the training set and 0.79 on the test set). A potential explanation could be that the severe class has a limited number of data points, but our random forest classifier for the severe class perfumed well. These results suggest that the best approach is a multi-class predictor.

D. Multi-Class Deep Neural Network Classifiers Using the Full Feature Set

Figure 3:
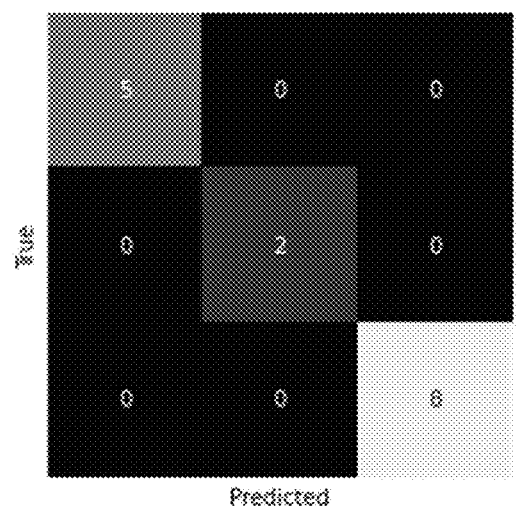
FIG. 3 illustrates full-feature multi-class DNN model confusion matrix for the test split.

The multi-class DNN implemented using the full feature set had good metrics (Table 3). The precision, recall and F1 score of 100%, 100% and 1.00 in the test split. This indicates that the model is not overfitting, and validating our notion that this would generalize better than the binary models. The model's performance is supported by its confusion matrix (true class vs predicted) where it is possible to determine how well it can predict the three classes (FIG. 3).

The potential of a DNN classifier is that it adjusts multiple parameters to transform the inputs into outputs. This is very important because the vast number of parameters allows for the model to better identify hidden signals in the data. Also, DNN require hyperparameter tuning, such as learning rate, number of hidden layers and neurons per hidden layer, as well as the optimizer and activation function, which affect the performance of the model. By adjusting these hyperparameters and castrating a model capable of finding the hidden relationships in the data we were able to achieve such high results and construct a predictive multi-class system.

E. Reduced Feature Multi-Class Deep Neural Network Classifiers

The results of the DNN indicated that the multi-class had the highest performance. Based on this, we constructed a DNN using the 6 most important features identified by the random forest variable importance. This model was known as minimal DNN or mDNN. This model was constructed using the same architecture as the full feature set DNN. This model's performance in the training set and the test set (Table 4), revealed a significant difference in both precision and recall, such difference could indicate that although the 6 features were identified as the most relevant, it could be possible that all variables contribute to the hidden pattern that makes up the classification of the instances. This idea is supported by the differences in performance between the mDNN and the full feature classifier in both training and test splits (Tables 3 & 4). This is further supported by the comparison of the confusion matrices, where mDNN (FIG. 4A) misclassifies more instances than the full feature multiclass DNN (FIG. 3).

Figure 4:
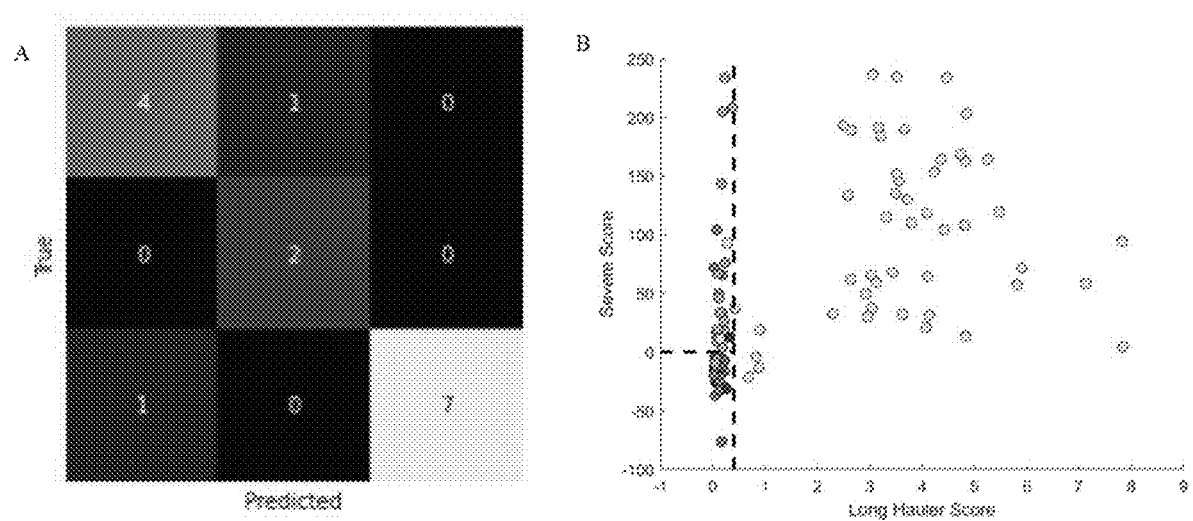
FIG. 4 illustrates classification abilities of the minimal Deep Neural Network (mDNN) and the discrimination heuristic generated using important variables. Panel A) The confusion matrix for the mDNN classifier denoting the presence of false positives for the severe and other classes. Panel B) Discrimination ability of the heuristic with reduced or most important features identified using Random Forest classifier. The dots represent the data points, where yellow are long haulers, green-severe, dark blue-mild/moderate and light blue-normal.

Moreover, we simplified our prediction model by feature engineering of two classification scores based on the top 5 informative features. First, a "Long Hauler Score" was defined as S1=(IFN-gamma+IL-2)/CCL4-MIP-1β. Second, "Severe Score" was defined as S2=(10*IL-10+IL-6)−(IL-2+IL8). Using a combined heuristic to first classify the Long Haulers (S1>0.4) and second the severe COVID-19 patients (S2>0), we obtained a sensitivity of 97% for Long Haulers with a 100% specificity and a sensitivity of 88% for severe patients with a specificity of 96% (FIG. 4B).

IV. DISCUSSION

Individuals infected with SARS-Cov2 exert distinct severity patterns which have been associated with different immune activation profiles. Interestingly, in some cases longer times are required to experience full recovery, representing a particular pathological type recently described as long-COVID or long haulers (LH). The scientific evidence generated during the last months strongly supports that the different outcomes on COVID-19 patients are determined by the immune mechanisms activated in response to the viral infection.

The immune response to SARS-Cov2 induces a release of different molecules with inflammatory properties such as cytokines and chemokines. This event, known as cytokine storm, is an immunopathological feature of COVID-19 and it has been associated with the severity of the disease. The increase in blood concentrations of different cytokines and chemokines such as IL-6, IL-8, IL-10, TNF-α, IL-1p, IL-2, IP-10, MCP-1, CCL3, CCL4, and CCL5 has been described for COVID-19 patients (4). Some of these molecules have been proposed as biomarkers to monitor the clinical evolution and to determine treatment selection for COVID-19 patients. Nevertheless, it is important to consider that some of these molecules function in a context dependent manner, therefore the clinical relevance of analyzing single cytokine changes is limited.

One of the most important challenges during the pandemics is to avoid the saturation of the health systems, therefore the determination of predictive biomarkers that allow a better stratification of the patients is paramount. Even though cytokines such as IL-6 and IL-8 have been proposed as indicators of the disease severity, and in some studies they were strong and independent predictors of patient survival (6), their predictive value when analyzed alone is debatable (7). The generation of scores considering blood levels of cytokines and chemokines with different immunological functions incorporates the importance of the context-dependent function of these molecules.

In order to predict severe cases, a score was generated considering IL-10, IL-6, IL-2, and IL-8 blood concentrations. In this classification, severe cases are characterized by high IL-6 and IL-10 levels, both cytokines previously attributed to increase the immunopathogenesis of COVID-19 and predictive value in severe cases (6, 8). In different settings, IL-6 has been associated with oxidative stress, inflammation, endothelial dysfunction, and thrombogenesis (9-12) which are characteristic features of severe COVID-19 cases caused by excessive myeloid cell activation (13). Consistently, increased IL-10 levels interfere with appropriate T-cell responses, inducing T-cell exhaustion and regulatory T cell polarization leading to an evasion of the antiviral immune response (14). Furthermore, besides its anti-inflammatory function on T cells, in some settings IL-10 induces STAT1 activation and a pro-inflammatory response in type I IFN-primed myeloid cells (15, 16). Therefore, elevated levels of IL-6 and IL-10 promote myeloid cell activation, oxidative stress, endothelial damage, and dampens adequate T cell activation. Additionally, to strengthen the classification, the score presented here, differentiates the severe cases by the subtraction of IL-2 and IL-8, which are cytokines related to proper T cell activation (IL-2) and recruitment (IL-8).

According to the score generated for distinguishing LH, these patients are characterized by an increased IFN-γ and IL-2 and a reduced CCL4 production. In the context of a viral infection, the combination of IFN-γ and IL-2 would induce the activation of effector T cells with pro-inflammatory properties and the capacity of generating an effective immune response to eliminate the virus. However, LH are characterized by longer periods of time with clinical signs and symptoms such as fatigue and lung damage. This suggests that the inflammatory context created by these cytokines to induce T cell activation is not enough to generate an adequate anti-viral response without the proper recruitment signals to attract activated T cells. CCL4 signals through the receptor CCR5 to attract T cells to the site of inflammation and depending on the immune context, this molecule recruits differently activated T cells (17-19). Moreover, it was recently shown by single cell analysis a down regulation of CCL4 expression in peripheral myeloid cell compartments in patients with mild and severe COVID-19 (20). In LH, IFN-γ and IL-2 would create an immune context to induce Th1 polarization, but the low levels of CCL4 affect the recruitment of these cells impairing the antiviral response. The effect of increased IFN-γ and IL-2 on T cell activation is evident in the reduction of the percentage of exhausted (CD4+PD1+/CD8+PD1+) and regulatory T cells (FoxP3+) compared to healthy donors. Interestingly, there is an increase in the percentage of circulating CD4+ and CD8+ T cells expressing CTLA-4 in the LH group compared to healthy donors, which is a molecule that affects antigen presentation in secondary lymphoid organs, but its presence in circulating T cells may reflect a compensatory mechanisms to the low CCL4 levels in the LH group. CTLA-4 induced signaling in T cells upregulates the expression of the CCL4 receptor CCR5 (21, 22), in the LH group CTLA-4 upregulation suggests a failed attempt to increase the sensitivity of IFN-γ/IL-2 activated T cells to CCL4. Therefore, proper T cell activation (high IFN-γ+IL-2) but ineffective T cell recruitment (low CCL4) are characteristic features of the failed anti-viral response observed in the LH group supporting virus persistence. Additionally, increased IFN-γ promotes myeloid cell activation which is observed in the augmented percentage of inflammatory CD14+CD16+ monocytes in the LH group compared to healthy donors, supporting lymphopenia and virus persistence in these patients. This is supported by recent findings describing an increased gene expression in response to IFN-γ in mild and severe COVID-19 patients in peripheral myeloid cells (20) and the dysregulation in the balance of monocyte populations by the expansion of the monocyte subsets described in COVID-19 patients (23). Finally, we propose that long-lasting pulmonary damage observed in LH, is caused by a combination of factors including 1) longer virus persistence influenced by LH immune profile characterized by high IFN-γ and IL-2 levels inducing Th1 polarization which is ineffective with low CCL4-induced T cell recruitment, leading to an inflammatory myeloid cell activation; and 2) the immunopathological pulmonary effects consequence of this LH immune profile. Regarding the immunopathological effects of LH immune profile, using murine models it has been shown that high IFN-γ levels could affect the kinetics of the resolution of inflammation-induced lung injury as well as thrombus resolution (24, 25), which could be related to long-lasting symptoms of LH associated to pulmonary coagulopathy and immune-mediated tissue damage.

Interestingly, COVID-19 individuals (including LH, mild, severe) show high levels of CCL5, a chemoattractant that like CCL4 signals through CCR5. Indeed, the disruption of the CCL5-CCR5 pathway restores immune balance in critical COVID-19 patients (4). In the specific case of LH, despite the high concentrations of CCL5 a reduction on the CCL4-mediated recruitment of activated T cells is proposed. This could be related to different factors:

(1) Reduction of total recruitment signals in LH with low CCL4 concentrations.

(2) Different functional responses of CCL4 and CCL5 to polymorphic variants of the CCR5. Distinct functional features have been reported to CCR5 variants regarding binding avidity, receptor internalization, Ca++ influx and chemotactic activity (26). Even though, clear mechanistic differences between CCL4 and CCL5 interaction with CCR5 are missing, it has been suggested that is important to consider the knowledge gained on CCR5 polymorphisms in HIV/AIDS context (27).

(3) Signaling through alternative receptors for CCL5. Besides CCR5, CCL5 can signal through the receptors CCR1 and CCR3 (28) whereas CCL4 effects are restricted to CCL5. It has been shown that CCL4 can bind to CCR1 but is not able to induce the intracellular pathway necessary for activating the chemoattractant stimulus (28, 29). Therefore, CCL4 has been proposed as an antagonist of CCR1 (29), however further analysis of this needs to be performed. Interestingly, CCR1 is expressed on blood myeloid cells such as monocytes and neutrophils (28), and it is upregulated on COVID-19 patients (30). Additionally, high levels of IFN-γ (feature of LH) have been associated with an increase CCR1 expression on human neutrophils (31). Therefore, in LH, high levels of CCL5 (combined with low levels of potential CCR1-antagonist CCL4) leads to a higher recruitment of myeloid cells expressing CCR1.

VI. REFERENCES

1. L. Chen, H. Deng, H. Cui, J. Fang, Z. Zuo, J. Deng, Y. Li, X. Wang, L. Zhao Inflammatory responses and inflammation-associated diseases in organs. *Oncotarget* 9, 7204-7218 (2018).
2. S. Rasa, Z. Nora-Krukle, N. Henning et al. Chronic viral infections in myalgic encephalomyelitis/chronic fatigue syndrome (ME/CFS). *J Transl Med* 16, 268 (2018).
3. P. A. Mudd, J. S. Turner, A. Day, W. B. Alsoussi, Z. Liu, J. A. O'Halloran, R. M. Presti, B. K. Patterson, S. P. J. Whelen, A. Ellebedy. SARS-CoV-2 viral RNA shedding for more than 87 days in an individual with an impaired CD8+ T-cell response. *Front Immunol* (in press).
4. B. K. Patterson, H. Seethamraju, K. Dhody, M. J. Corley, K. Kazempour, J. P., Lalezari, A. P. Pang, C. Sugai, E. B. Francisco, A. Pise, H. Rodrigues, M. Ryou, H. L. Wu, G. M. Webb, B. S. Park, S. Kelly, N. Pourhassan, A. Lelic, L. Kdouh, M. Herrera, E. Hall, E. Aklin, L. Ndhlovu, J. B. Sacha. CCR5 inhibition in Critical COVID-19 Patients Decreases Inflammatory Cytokines, Increases CD8 T-Cells, and Decreases SARS-CoV2 RNA in Plasma by Day 14. *Int J Infect Dis* (2020) doi: 10.1016/j.ijid.2020.10.101
5. G. Coquillard, B. Patterson. HCV-Infected, Monocyte Lineage Reservoirs Differ in Individuals with or without HIV Co-Infection. *J Infect Dis* 2009; 200:947-954.
6. D. M. Del Valle, S. Kim-Schulze, H. H. Huang, N. D. Beckmann, S. Nirenberg, B. Wang, Y. Lavin, T. H. Swartz, D. Madduri, A. Stock, T. U. Marron, H. Xie, M. Patel, K. Tuballes, O. Van Oekelen, A. Rahman, P. Kovatch, J. A. Aberg, E. Schadt, S. Jagannath, M. Mazumdar, A. W. Charney, A. Firpo-Betancourt, D. R. Mendu, J. Jhang, D. Reich, K. Sigel, C. Cordon-Cardo, M. Feldmann, S. Parekh, M. Merad, S. Gnjatic, An inflammatory cytokine signature predicts COVID-19 severity and survival. *Nat Med*, 26, 1636-1643 (2020).
7. S. M. Russell, A. Alba-Patiño, E. Baron, M. Borges, M. Gonzalez-Freire, & R. de la Rica. Biosensors for Managing the COVID-19 Cytokine Storm: Challenges Ahead. *ACS Sens*, 5, 1506-1513.
8. S. K. Dhar, K, V., S. Damodar, S. Gujar & M. Das, IL-6 and IL-10 as redictors of disease severity in COVID 19 patients: Results from Meta-analysis and Regression. *medRxiv*, 2020.2008.2015.20175844. https://doi.org/10.1101/2020.08.15.20175844
9. T. Hou, Tieu, B. C., S. Ray, A. Recinos Iii, R. Cui, R. G. Tilton, & A. R. Brasier. Roles of IL-6-gp130 Signaling in Vascular Inflammation. *Curr Cardiol Rev*, 4(3), 179-192. https://doi.org/10.2174/157340308785160570
10. J. Lee, S. Lee, H. Zhang, M. A. Hill, C. Zhang, & Y. Park. Interaction of IL-6 and TNF-α contributes to endothelial dysfunction in type 2 diabetic mouse hearts. *PLoS One*, 12(11), e0187189. https://doi.org/10.1371/journal.pone.0187189
11. V. Roldan, F. Marin, A. D. Blann, A. Garcia, P. Marco, F. Sogorb, & G. Y. Lip. Interleukin-6, endothelial activation and thrombogenesis in chronic atrial fibrillation. *Eur Heart J*, 24(14), 1373-1380. https://doi.org/10.1016/s0195-668x(03)00239-2
12. S. Wassmann, M. Stumpf, K. Strehlow, A. Schmid, B. Schieffer, M. Bohm, & G. Nickenig. Interleukin-6 induces oxidative stress and endothelial dysfunction by overexpression of the angiotensin II type 1 receptor. *Circ Res*, 94(4), 534-541. https://doi.org/10.1161/01.res.0000115557.25127.8d
13. D. McGonagle, K. Sharif, A. O'Regan, & C. Bridgewood. The Role of Cytokines including Interleukin-6 in COVID-19 induced Pneumonia and Macrophage Activation Syndrome-Like Disease. *Autoimmun Rev*, 19(6), 102537. https://doi.org/10.1016/j.autrev.2020.102537
14. J. M. Rojas, M. Avia, V. Martin, & N. Sevilla. IL-10: A Multifunctional Cytokine in Viral Infections. *J Immunol Res*, 2017, 6104054. https://doi.org/10.1155/2017/6104054
15. H. MON. Pro-Inflammatory Signaling by IL-10 and IL-22: Bad Habit Stirred Up by Interferons? *Front Immunol*, 4, 18. https://doi.org/10.3389/fimmu.2013.00018
16. M. N. Sharif, I. Tassiulas, Y. Hu, I. Mecklenbrauker, A. Tarakhovsky, & L. B. Ivashkiv. IFN-alpha priming results in a gain of proinflammatory function by IL-10: implications for systemic lupus erythematosus pathogenesis. *J Immunol*, 172(10), 6476-6481. https://doi.org/10.4049/jimmunol.172.10.6476
17. J. Y. Liu, F. Li, L. P. Wang, X. F. Chen, D. Wang, L. Cao, Y. Ping, S. Zhao, B. Li, S. H. Thorne, B. Zhang, P. Kalinski, & Y. Zhang. CTL-vs Treg lymphocyte-attracting chemokines, CCL4 and CCL20, are strong reciprocal predictive markers for survival of patients with oesophageal squamous cell carcinoma. *Br J Cancer*, 113(5), 747-755. https://doi.org/10.1038/bjc.2015.290

18. N. Mukaida, S. I. Sasaki, & T. Baba. CCL4 Signaling in the Tumor Microenvironment. *Adv Exp Med Biol,* 1231, 23-32. https://doi.org/10.1007/978-3-030-36667-4_3
19. M. N. Sharif, I. Tassiulas, Y. Hu, I. Mecklenbrauker, A. Tarakhovsky, & L. B. Ivashkiv. IFN-alpha priming results in a gain of proinflammatory function by IL-10: implications for systemic lupus erythematosus pathogenesis. *J Immunol,* 172(10), 6476-6481. https://doi.org/10.4049/jimmunol.172.10.6476
20. G. Xu, F. Qi, H. Li, Q. Yang, H. Wang, X. Wang, X. Liu, J. Zhao, X. Liao, Y. Liu, L. Liu, S. Zhang, & Z. Zhang. The differential immune responses to COVID-19 in peripheral and lung revealed by single-cell RNA sequencing. *Cell Discov,* 6, 73. https://doi.org/10.1038/s41421-020-00225-2
21. K. Knieke, H. Hoff, F. Maszyna, P. Kolar, A. Schrage, A. Hamann, G. F. Debes, M. C. Brunner-Weinzierl. CD152 (CTLA-4) determines CD4 T cell migration in vitro and in vivo. *PLoS One,* 4, e5702. (2009). https://doi.org/10.1371/journal.pone.0005702
22. K. Knieke, H. Lingel, K. Chamaon, & M. C. Brunner-Weinzierl. Migration of Th1 lymphocytes is regulated by CD152 (CTLA-4)-mediated signaling via PI3 kinase-dependent Akt activation. *PLoS One,* 7(3), e31391. (2012). https://doi.org/10.1371/journal.pone.0031391
23. W. Shi, X. Liu, Q. Cao, P. Ma, W. Le, L. Xie, J. Ye, W. Wen, H. Tang, W. Su, Y. Zheng, & Y. Liu. High-dimensional single-cell analysis reveals the immune characteristics of COVID-19. *Am J Physiol Lung Cell Mol Physiol.* https://doi.org/10.1152/ajplung.00355.2020
24. J. R. Mock, M. K. Tune, C. F. Dial, J. Torres-Castillo, R. S. Hagan, & C. M. Doerschuk. Effects of IFN-γ on immune cell kinetics during the resolution of acute lung injury. *Physiol Rep,* 8(3), e14368. https://doi.org/10.14814/phy2.14368
25. M. Nosaka, Y. Ishida, A. Kimura, Y. Kuninaka, M. Inui, N. Mukaida, & T. Kondo. Absence of IFN-γ accelerates thrombus resolution through enhanced MMP-9 and VEGF expression in mice. *J Clin Invest,* 121(7), 2911-2920. https://doi.org/10.1172/jci40782
26. H. F. Dong, K. Wigmore, M. N. Carrington, M. Dean, J. A. Turpin, & O. M. Howard. Variants of CCR5, which are permissive for HIV-1 infection, show distinct functional responses to CCL3, CCL4 and CCL5. *Genes Immun,* 6(7), 609-619. https://doi.org/10.1038/sj.gene.6364247
27. R. K. Mehlotra. Chemokine receptor gene polymorphisms and COVID-19: Could knowledge gained from HIV/AIDS be important? *Infect Genet Evol,* 85, 104512. https://doi.org/10.1016/j.meegid.2020.104512
28. C. E. Hughes, & R. J. B. Nibbs. A guide to chemokines and their receptors. *Febs j,* 285(16), 2944-2971. https://doi.org/10.1111/febs.14466
29. H. Gaertner, O. Lebeau, I. Borlat, F. Cerini, B. Dufour, G. Kuenzi, A. Melotti, R. J. Fish, R. Offord, J. Y. Springael, M. Parmentier, & O. Hartley. Highly potent HIV inhibition: engineering a key anti-HIV structure from PSC-RANTES into MIP-1 beta/CCL4. *Protein Eng Des Sel,* 21(2), 65-72. https://doi.org/10.1093/protein/gzm079
31. P. R. Ray, A. Wangzhou, N. Ghneim, M. S. Yousuf, C. Paige, D. Tavares-Ferreira, J. M. Mwirigi, S. Shiers, I. Sankaranarayanan, A. J. McFarland, S. V. Neerukonda, S. Davidson, G. Dussor, M. D. Burton, & T. J. Price. A pharmacological interactome between COVID-19 patient samples and human sensory neurons reveals potential drivers of neurogenic pulmonary dysfunction. *Brain Behav Immun,* 89, 559-568. https://doi.org/10.1016/j.bbi.2020.05.078
32. R. Bonecchi, N. Polentarutti, W. Luini, A. Borsatti, S. Bernasconi, M. Locati, C. Power, A. Proudfoot, T. N. Wells, C. Mackay, A. Mantovani, & S. Sozzani. Up-regulation of CCR1 and CCR3 and induction of chemotaxis to CC chemokines by IFN-gamma in human neutrophils. *J Immunol,* 162(1), 474-479.

VII. TREATMENT OF LONG HAULERS FOR CHRONIC COVID-19

Long Hauler patients suffering from chronic COVID-19 were treated for 2 weeks with 300 mg of Maraviroc (Selzentry) twice a day. It was observed that treatment alleviated or completely resolved symptoms in long haulers that was further reflected in reduced long hauler Indices. The results are provided below, which provide patient profiles and LHI (long haul index as determined using the panel described in the preceding example. LHI is also referred to as "Long Hauler Score" or S1, where S1=(IFN-gamma+IL 2)/CCL4-MIP-1β.

Decreased CCL5/RANTES in Chronic COVID patients successfully treated [decreased log hauler index (HLI)] with the CCR5 antagonist maraviroc

| Average (pg/ml) | TNF-α | IL-4 | IL-13 | IL-2 | GM-CSF | sCD40L | CCL5 (RANTES) | |
|---|---|---|---|---|---|---|---|---|
| Normals | 9.09 | 4.18 | 3.94 | 6.17 | 51.27 | 7192.39 | 10781.84 | |
| AB1 | 7.75 | 11.06 | <3.07 | 12.57 | 6.02 | 13488. | 13082.39 | |
| AB2 | 17.13 | 4.12 | 4.35 | 2.15 | 15.09 | 12631. | 12261.36 | |
| Average (pg/ml) | CCL3 (MIP-1α) | IL-6 | IL-10 | IFN-γ | VEGF | IL-8 | CCL4 (MIP-1β) | LHI |
| Normals | 22.82 | 2.21 | 0.67 | 1.94 | 9.32 | 16.87 | 76.84 | 0.75 |
| AB1 | 87.65 | 10.88 | 7.90 | 48.78 | 60.41 | <15.74 | 15.52 | 4.0 |
| AB2 | <1.22 | <0.6 | <0.61 | <0.92 | 22.98 | 18.37 | 8.43 | 0.3 |
| Average (pg/ml) | TNF-α | IL-4 | IL-13 | IL-2 | GM-CSF | sCD40L | CCL5 (RANTES) | |
| Normals | 9.09 | 4.18 | 3.94 | 6.17 | 51.27 | 7192.3 | 10781.84 | |
| | 17.86 | <5.02 | 5.56 | 33.94 | 10.40 | 8980. | 14334.86 | |
| | 17.50 | <1.22 | 4.22 | 4.89 | 9.07 | 41374. | 10011.91 | |

-continued

Decreased CCL5/RANTES in Chronic COVID patients successfully treated [decreased log hauler index (HLI)] with the CCR5 antagonist maraviroc

| Average (pg/ml) | CCL3 (MIP-1α) | IL-6 | IL-10 | IFN-γ | VEGF | IL-8 | CCL4 (MIP-1β) | |
|---|---|---|---|---|---|---|---|---|
| Normals | 22.82 | 2.21 | 0.67 | 1.94 | 9.32 | 16.87 | 76.84 | 0.75 |
| | <34.82 | <4.66 | <1.20 | <7.30 | 39.00 | <3.82 | 3.62 | 11.4 |
| | <45.08 | <3.60 | <2.49 | <7.77 | 31.62 | <9.98 | 9.79 | 1.3 |

| Average (pg/ml) | TNF-α | IL-4 | IL-13 | IL-2 | GM-CSF | sCD40L | CCL5 (RANTES) |
|---|---|---|---|---|---|---|---|
| Normals | 9.09 | 4.18 | 3.94 | 6.17 | 51.27 | 7192.39 | 10781.84 |
| ZH | 9.8 | 16.34 | 3.55 | 10.32 | 5.34 | 9980.3 | 15091.68 |
| ZH 2 | 2.15 | 8.09 | 1.46 | 9.78 | 1.79 | 10522.7 | 7507.99 |
| JM | 5.2 | 20.23 | 2.44 | 12.05 | 4.52 | 12162.3 | 25617.81 |
| JM 2 | 4.29 | 31.94 | 1.67 | 24.83 | 1.8 | 18327.1 | 15013.59 |

| Average (pg/ml) | CCL3 (MIP-1α) | IL-6 | IL-10 | IFN-γ | VEGF | IL-8 | CCL4 (MIP-1β) |
|---|---|---|---|---|---|---|---|
| Normals | 22.82 | 2.21 | 0.67 | 1.94 | 9.32 | 16.87 | 76.84 |
| ZH | 173.67 | 42.42 | 11.38 | 112.03 | 12.12 | 15.45 | 34.35 |
| ZH 2 | 58.64 | 9.64 | 7.53 | 51.25 | 6.41 | 3.51 | 10.34 |
| JM | 202.36 | 52.8 | 14.33 | 136.15 | 40.93 | 15.45 | 46.18 |
| JM 2 | 233.05 | 54.01 | 30.29 | 170.88 | 74.36 | 6.16 | 65.45 |

Because long haulers have a distinct immunologic profile from patients with active COVID as defined by the long hauler index described herein, we were surprised that CCR5 antagonism would benefit these patients and relieve symptoms in these individuals. Since it has been hypothesized that long haulers may have persistent SARS-CoV2 in hidden reservoirs, one would presume anti-virals would be the drug of choice which would teach away from the use of immune modulators like CCR5 antagonists or immunosuppressives like dexamethasone.

Figure 5:
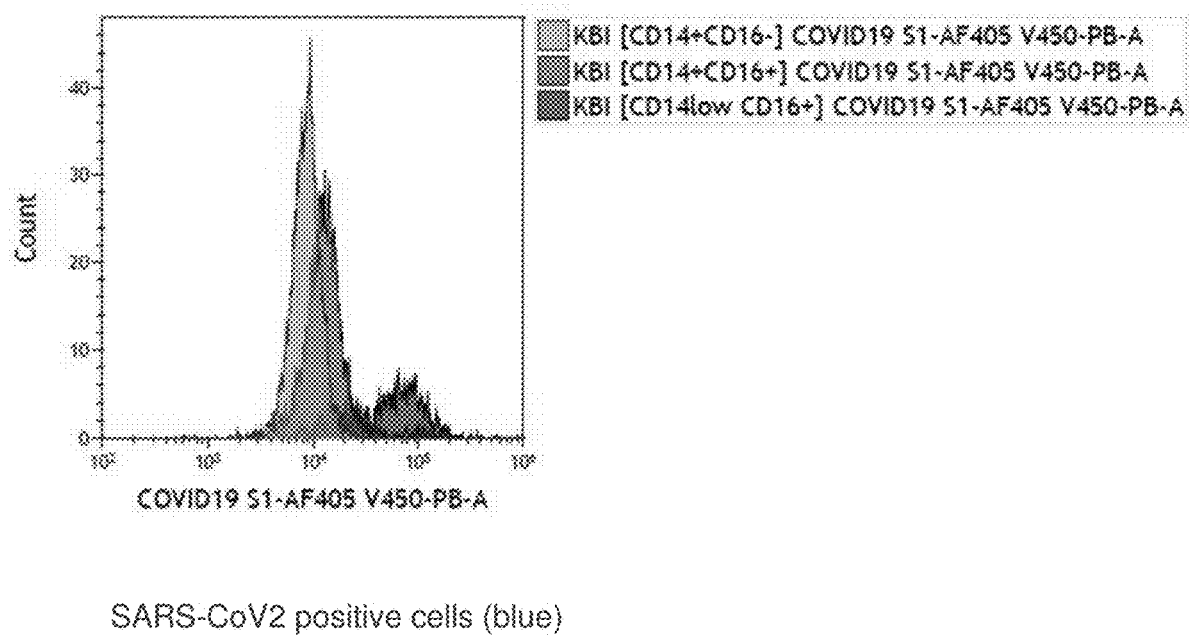
FIG. 5 shows persistent SARS-CoV-2 antigen in CD14Lo, CD16+ monocytes that may be the source of Chronic COVID inflammation.

Since "long haulers" clearly represent an immunologically distinct patient (FIG. 4B) from active COVID-19, it would not be obvious that treatments that ameliorate the immunologic abnormalities in active COVID would necessarily be effective in "long haulers". In fact, the discovery that SARS-CoV-2 protein is still presented in antigen presenting cells (CD14Lo, CD16+)(see FIG. 5) would lead to "long hauler" specific therapy. FIG. 5 shows persistent SARS-CoV-2 antigen in CD14Lo, CD16+ monocytes that may be the source of Chronic COVID inflammation.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of treating a long-hauler subject for chronic COVID-19, the method comprising:
   administering to the long-hauler subject a CCR5/CCL5 interaction inhibitor to treat the subject for chronic COVID-19,
   wherein the CCR5/CCL5 interaction inhibitor comprises a CCR5 antagonist.

2. The method according to claim 1, wherein the CCR5 antagonist is a specific binding member for CCR5.

3. The method according to claim 2, wherein the specific binding member for CCR5 is an antibody that specifically binds to CCR5.

4. The method according to claim 3, wherein the antibody that specifically binds to CCR5 is a humanized monoclonal antibody.

5. The method according to claim 4, wherein the antibody that specifically binds to CCR5 is leronlimab (PRO 140).

6. The method according to claim 1, wherein the CCR5 antagonist is a small molecule.

7. The method according to claim 6, wherein the small molecule is maraviroc.

8. The method according to claim 6, wherein the small molecule is cenicriviroc.

9. The method according to claim 6, wherein the small molecule is OB-002.

10. The method according to claim 6, wherein the small molecule is BMS-813160.

11. The method according to claim 1, further comprising administering an antiviral agent to the long-hauler subject.

12. The method according to claim 1, further comprising administering an immunomodulatory agent to the subject, wherein the immunomodulatory agent is selected from the group consisting of: a corticosteroid, an interferon, an interleukin-1 inhibitor, an interleukin-6 inhibitor, and a kinase inhibitor.

13. The method according to claim 1, wherein the treating comprises a reduction in a Long Hauler Score (S1) of the subject as compared to the S1 before the administering.

14. The method according to claim 1, wherein the treating comprises a reduction in CCL5 level in the subject as compared to CCL5 level before the administering.

15. A method of treating a long-hauler subject for chronic COVID-19, the method comprising:
   administering to the long-hauler subject a CCR5/CCL5 interaction inhibitor to treat the subject for chronic COVID-19,
   wherein the CCR5/CCL5 interaction inhibitor comprises a CCL5 antagonist.

16. The method according to claim 15, wherein the CCL5 antagonist is an antibody that specifically binds to CCL5.

17. The method according to claim 15, wherein the treating comprises a reduction in a Long Hauler Score (S1) of the subject as compared to the S1 before the administering.

18. The method according to claim 15, wherein the treating comprises a reduction in CCL5 level in the subject as compared to CCL5 level before the administering.

* * * * *

UNITED STATES PATENT AND TRADEMARK OFFICE
CERTIFICATE OF CORRECTION

| | |
|---|---|
| PATENT NO. | : 11,402,391 B2 |
| APPLICATION NO. | : 17/351055 |
| DATED | : August 2, 2022 |
| INVENTOR(S) | : Patterson et al. |

It is certified that error appears in the above-identified patent and that said Letters Patent is hereby corrected as shown below:

In the Specification

Please replace "IL-1p" with -- IL-1β -- (Column 29, Line 33).

Signed and Sealed this
Sixth Day of September, 2022

Katherine Kelly Vidal
*Director of the United States Patent and Trademark Office*